US011421002B2

(12) United States Patent
Mori et al.

(10) Patent No.: US 11,421,002 B2
(45) Date of Patent: Aug. 23, 2022

(54) MODIFIED HSV GB PROTEIN AND HSV VACCINE INCLUDING SAME

(71) Applicant: KM Biologics Co., Ltd., Kumamoto (JP)

(72) Inventors: Hiroaki Mori, Kumamoto (JP); Tomohiro Nishimura, Kumamoto (JP); Hiroyuki Shimizu, Ageo (JP); Miyuki Matsumoto, Kikuyo-machi (JP)

(73) Assignee: KM BIOLOGICS CO., LTD., Kumanmoto (JP)

( * ) Notice: Subject to any disclaimer, the term of this patent is extended or adjusted under 35 U.S.C. 154(b) by 0 days.

(21) Appl. No.: 16/641,432

(22) PCT Filed: Aug. 29, 2018

(86) PCT No.: PCT/JP2018/032020
§ 371 (c)(1),
(2) Date: Feb. 24, 2020

(87) PCT Pub. No.: WO2019/044927
PCT Pub. Date: Mar. 7, 2019

(65) Prior Publication Data
US 2020/0299334 A1    Sep. 24, 2020

(30) Foreign Application Priority Data

Aug. 30, 2017   (JP) .............. JP2017-165684

(51) Int. Cl.
*C07K 14/005* (2006.01)
*A61P 31/22* (2006.01)
*A61K 39/245* (2006.01)

(52) U.S. Cl.
CPC .......... *C07K 14/005* (2013.01); *A61K 39/245* (2013.01); *A61P 31/22* (2018.01)

(58) Field of Classification Search
CPC ............... C07K 14/005; A61K 39/245; A61K 2039/55561; A61K 2039/55572; A61K 39/12; A61P 31/22; A61P 37/04; C12N 2710/16622; C12N 2710/16634; C12N 15/09; C12N 2710/16671
See application file for complete search history.

(56) References Cited

U.S. PATENT DOCUMENTS

2010/0272752 A1* 10/2010 Spector .................. A61K 39/12
424/207.1
2020/0239549 A1* 7/2020 Mori .................... A61K 39/395

FOREIGN PATENT DOCUMENTS

| EP | 0170169 A | 2/1986 |
| EP | 2308895 A1 | 4/2011 |
| JP | 61-28391 A | 2/1986 |
| JP | 2007246531 A | 9/2007 |

OTHER PUBLICATIONS

Bowie JU, Reidhaar-Olson JF, Lim WA, Sauer RT. Deciphering the message in protein sequences: tolerance to amino acid substitutions. Science. Mar. 16, 1990;247(4948):1306-10. (Year: 1990).*
Winkler K, Kramer A, Küttner G, Seifert M, Scholz C, Wessner H, Schneider-Mergener J, Höhne W. Changing the antigen binding specificity by single point mutations of an anti-p24 (HIV-1) antibody. J Immunol. Oct. 15, 2000;165(8):4505-14. (Year: 2000).*
Kussie PH, Parhami-Seren B, Wysocki LJ, Margolies MN. A single engineered amino acid substitution changes antibody fine specificity. J Immunol. Jan. 1, 1994;152(1): 146-52. (Year: 1994).*
Sirin S, Apgar JR, Bennett EM, Keating AE. AB-Bind: Antibody binding mutational database for computational affinity predictions. Protein Sci. Feb. 2016;25(2):393-409. Epub Nov. 6, 2015. (Year: 2016).*
Weed DJ, Dollery SJ, Komala Sari T, Nicola AV. Acidic pH Mediates Changes in Antigenic and Oligomeric Conformation of Herpes Simplex Virus gB and Is a Determinant of Cell-Specific Entry. J Virol. Aug. 16, 2018;92(17):e01034-18. (Year: 2018).*
Bender FC, Samanta M, Heldwein EE, de Leon MP, Bilman E, Lou H, Whitbeck JC, Eisenberg RJ, Cohen GH. Antigenic and mutational analyses of herpes simplex virus glycoprotein B reveal four functional regions. J Virol. Apr. 2007;81(8):3827-41. Epub Jan. 31, 2007. (Year: 2007).*
Qadri I, Gimeno C, Navarro D, Pereira L. Mutations in conformation-dependent domains of herpes simplex virus 1 glycoprotein B affect the antigenic properties, dimerization, and transport of the molecule. Virology. Jan. 1991;180(1):135-52. (Year: 1991).*
Kousoulas KG, Huo B, Pereira L. Antibody-resistant mutations in cross-reactive and type-specific epitopes of herpes simplex virus 1 glycoprotein B map in separate domains. Virology. Oct. 1988;166(2):423-31. (Year: 1988).*
Cairns TM, Huang ZY, Whitbeck JC, Ponce de Leon M, Lou H, Wald A, Krummenacher C, Eisenberg RJ, Cohen GH. Dissection of the antibody response against herpes simplex virus glycoproteins in naturally infected humans. J Virol. Nov. 2014;88(21):12612-22. Epub Aug. 20, 2014. (Year: 2014).*
Chentoufi AA, Binder NR, Berka N, Durand G, Nguyen A, Bettahi I, Maillere B, BenMohamed L. Asymptomatic human CD4+ cytotoxic T-cell epitopes identified from herpes simplex virus glycoprotein B. J Virol. Dec. 2008;82(23):11792-802. Epub Sep. 17, 2008. (Year: 2008).*
Pereira L, Ali M, Kousoulas K, Huo B, Banks T. Domain structure of herpes simplex virus 1 glycoprotein B: neutralizing epitopes map in regions of continuous and discontinuous residues. Virology. Sep. 1989;172(1):11-24. (Year: 1989).*
Li W, Minova-Foster TJ, Norton DD, Muggeridge MI. Identification of functional domains in herpes simplex virus 2 glycoprotein B. J Virol. Apr. 2006;80(8):3792-800. (Year: 2006).*
Roizman et al., "Fields Virology 5th ed., Herpes simplex viruses", Lippincott Williams & Wilkins, Philadelphia, P.A., 2007, pp. 2501-2569.

(Continued)

*Primary Examiner* — Rachel B Gill
(74) *Attorney, Agent, or Firm* — Pillsbury Winthrop Shaw Pittman LLP

(57) ABSTRACT

A modified protein of a herpes simplex virus (HSV) envelope glycoprotein B (gB), in which at least one non-neutralizing antibody-inducing epitope (non-neutralizing epitope) present in domain IV and domain I of wild-type HSV gB is inactivated (de-epitoped).

14 Claims, 17 Drawing Sheets

Specification includes a Sequence Listing.

(56) References Cited

OTHER PUBLICATIONS

Hashido et al., "An epidemiologic study of herpes simplex virus type 1 and 2 infection in Japan based on type-specific serological assays", Epidemiol Infect., Mar. 1998120(2), pp. 179-186.
Kawaguchi, "Herpes simplex virus (HSV)", Virus, 2010, vol. 60(2), pp. 187-196.
Herold et al., "Glycoprotein C-independent binding of herpes simplex virus to cells requires cell surface heparan sulphate and glycoprotein B.", J Gen Virol, 1994, 75 (Pt 6), pp. 1211-1222.
Herold et al., "Glycoprotein C of herpes simplex virus type 1 plays a principal role in the adsorption of virus to cells and in infectivity", J Virol, 1991, 65(3), pp. 1090-1098.
Arii et al., "Non-muscle myosin IIA is a functional entry receptor for herpes simplex virus-1", Nature, 2010, vol. 467, pp. 859-862.
Satoh et al., "PILRalpha is a herpes simplex virus-1 entry coreceptor that associates with glycoprotein B.", Cell, 2008, vol. 132, pp. 935-944.
Suenaga et al., "Myelin-associated glycoprotein mediates membrane fusion and entry of neurotropic herpesviruses.", Proc Natl Acad Sci USA, 2010)0, vol. 107, pp. 866-871.
Geraghty et al., "Entry of alphaherpesviruses mediated by poliovirus receptor-related protein 1 and poliovirus receptor.", Science, 1998, vol. 280, pp. 1618-1620.
Montgomery et al., "Herpes simplex virus-1 entry into cells mediated by a novel member of the TNF/NGF receptor family.", Cell, 1996, vol. 87, pp. 427-436.
Shukla et al., et al., "A novel role for 3-O-sulfated heparan sulfate in herpes simplex virus 1 entry.", Cell, 1999, vol. 99, pp. 13-22.
Eisenberg et al., "Herpes virus fusion and entry: a story with manycharacters.". Viruses, 2012, vol. 4, pp. 800-832.
Tobin et al., "Deceptive imprinting and immune Refocusing in vaccine design", Vaccine, 2008, vol. 26, pp. 6189-6199.
Garrity et al., "Refocusing neutralizing antibody response by targeted dampening of an immunodominant epitope.", The Journal of Immunology, 1997, vol. 159(1), pp. 279-289.
Bender et al., "Antigenic and mutational analyses of herpes simplex virus glycoprotein B reveal four functional regions", J. Virol., 2007, vol. 81(8), pp. 3827-3841.
Yu et al., "Replacing the decoy epitope of PCV2b capsid protein with a protective epitope enhances efficacy of PCV2b vaccine". Vaccine, 2016, vol. 34(50), pp. 6358-6366.
Cleveland et al., "Immunogenic and antigenic dominance of a nonneutralizing epitope over a highly conserved neutralizing epitope in the gp41 envelope glycoprotein of human immunodeficiency virus type 1: its deletion leads to a strong neutralizing response", Virology, 2000, vol. 266(1), pp. 66-78.
Nara et al., "How can vaccines against influenza and other viral diseases be made more effective?", PLoS Biol., 2010, vol. 8(12), e1000571, pp. 1-4.
Highlander et al., "Identification of mar mutations in herpes simplex virus type 1 glycoprotein B which alter antigenic structure and function in virus penetration", J. Virol., 1989, vol. 63(2), pp. 730-738.
Schmidt-Chanasit et al., "A 12-year molecular survey of clinical herpes simplex virus type 2 isolates demostrates the circulation of clade A and B strains in Germany", J Clin. Virol., 2010, vol. 48, pp. 208-211.
Heldwein et al., "Crystal structure of glycoprotein B from herpes simplex virus 1", Science, 2006, vol. 313(5784), pp. 217-220.
Zwaagstra et al., "The nucleotide sequence of herpes simplex virus type 2 (333) glycoprotein gB2 and analysis of predicted antigenic sites", Can. J Microbiol, 1987, vol. 33(10), pp. 879-887.
Hannah et al., "Mutational evidence of internal fusion loops in herpes simplex virus glycoprotein B", J. Virol., 2007, vol. 81(9), pp. 4858-4865.
Vitu et al., "Extensive mutagenesis of the HSV-1 gB ectodomain reveals remarkable stability of its postfusion form", J. Mol. Biol., 2013, vol. 425(11), pp. 2056-2071.
De Taeye et al., "Immunogenicity of Stabilized HIV-1 Envelope Trimers with Reduced Exposure of Non-neutralizing Epitopes", Cell, 2015, vol. 163(7), pp. 1702-1715.
Fang et al., "Enhanced immunogenicity of the modified GP5 of porcine reproductive and respiratory syndrome virus", Virus Genes, 2006, vol. 32(1), pp. 5-11.
Patent Cooperation Treaty, International Search Report for PCT/JP2018/032020, dated Nov. 27, 2018, pp. 1-3.
Patent Cooperation Treaty, International Preliminary Report on Patentability for PCT/JP2018/032020, dated Mar. 3, 2020, pp. 1-7.
European Patent Office, Extended European Search Report issued in EP Patent Application No. 18851447.5, dated May 11, 2021, pp. 1-8.

* cited by examiner

gB1-705 V50 (bcev50)

Symptom score vs Days after infection (days)
- Saline
- 1μg
- 0.3μg
- 0.1μg
- 0.03μg (B)

gB1-705 V50 (bcev50)

Symptom score vs Days after infection (days)
- Saline
- 1μg
- 0.3μg
- 0.1μg
- 0.03μg (A)

Neutralizing antibody-inducing activity (HSV-2)

(B)

Anti-gB binding antibody-inducing activity (A)

```
HSV1    :MHQGAPSWGRRWFVVWALLGLTLGVLVASAAPTSPGTP---GVAAATQAANGGPATPAPP  27
HSV2    :MRGGGLICALVVGALVAAVASA----------APAAPAAPRASGGVAATVAANGGPASRPPP  30

HSV1  28:PLGAAPTGDPKPKKNKKPKNPTPPRPAGGNATVAAGHATLREHLRDIKAENTDANFYVCP  87
HSV2  31:VPSPATTKARKRKTKKPPKRPEATPPPDANATVAAGHATLRAHLREIKVENADAQFYVCP  90

HSV1  88:PPTGATVVQFEQPRRCPTRPEGQNYTEGIAVVFKENIAPYKFKATMYYKDVTVSQVWFGH  147
HSV2  91:PPTGATVVQFEQPRRCPTRPEGQNYTEGIAVVFKENIAPYKFKATMYYKDVTVSQVWFGH  150

HSV1 148:RYSQFMGIFEDRAPVPFEEVIDKINAKGVCRSTAKYVRNNLETTAFHRDDHETDMELKPA  207
HSV2 151:RYSQFMGIFEDRAPVPFEEVIDKINAKGVCRSTAKYVRNNMETTAFHRDDHETDMELKPA  210

HSV1 208:NAATRTSRGWHTTDLKYNPSRVEAFHRYGTTVNCIVEEVDARSVYPYDEFVLATGDFVYM  267
HSV2 211:KVATRTSRGWHTTDLKYNPSRVEAFHRYGTTVNCIVEEVDARSVYPYDEFVLATGDFVYM  270

HSV1 268:SPFYGYREGSHTEHTTYAADRFKQVDGFYARDLTTKARATAPTTRNLLTTPKFTVAWDWV  327
HSV2 271:SPFYGYREGSHTEHTSYAADRFKQVDGFYARDLTTKARATSPTTRNLLTTPKFTVAWDWV  330

HSV1 328:PKRPSVCTMTKWQEVDEMLRSEYGGSFRFSSDAISTTFTTNLTEYPLSRVDLGDCIGKDA  387
HSV2 331:PKRPAVCTMTKWQEVDEMLRAEYGGSFRFSSDAISTTFTTNLTQYSLSRVDLGDCIGRDA  390

HSV1 388:RDAMDRIFARRYNATHIKVGQPQYYQANGGFLIAYQPLLSNTLAELYVREHLREQSRKPP  447
HSV2 391:REAIDRMFARKYNATHIKVGQPQYYLATGGFLIAYQPLLSNTLAELYVREYMREQDRKPR  450

HSV1 478:NPTPPPP--GASANASVERIKTTSSIEFARLQFTYNHIQRHVNDMLGRVAIAWCELQNHE  505
HSV2 451:NATPAPLREAPSANASVERIKTTSSIEFARLQFTYNHIQRHVNDMLGRIAVAWCELQNHE  510

HSV1 506:LTLWNEARKLNPNAIASVTGRRVSARMLGDVMAVSTCVPVAADNVIVQNSMRISSRPGA  565
HSV2 511:LTLWNEARKLNPNAIASATVGRRVSARMLGDVMAVSTCVPVAPDNVIVQNSMRVSSRPGT  570

HSV1 566:CYSRPLVSFRYEDQGPLVEGQLGENNELRLTRDAIEPCTVGHRRYFTPGGGYVYFEEYAY  625
HSV2 571:CYSRPLVSFRYEDQGPLIEGQLGENNELRLTRDALEPCTVGHRRYFIFGGGYVYFEEYAY  630

HSV1 626:SHQLSRADITTVSTFIDLNITMLEDHEFVPLEVYTRHEIKDSGLLDYTEVQRRNQLHDLR  685
HSV2 631:SHQLSRADVTTVSTFIDLNITMLEDHEFVPLEVYTRHEIKDSGLLDYTEVQRRNQLHDLR  690

HSV1 686:FADIDTVIHADANAAMFAGLGAFFEGMGDLGRAVGKVVMGIVGGVVSAVSGVSSFMSNPF  745
HSV2 691:FADIDTVIRADANAAMFAGLCAFFEGMGDLGRAVGKVVMGVVGGVVSAVSGVSSFMSNPF  750

HSV1 746:GALAVGLLVLAGLAAFFAFRYVMRLQSNPMKALYPLTTKELKNFTNPDASGEGEE---G  802
HSV2 751:GALAVGLLVLAGLVAAFFAFRYVLQLQRNPMKALYPLTTKELKTSDPGGVGGEGEEGAEG  810

HSV1 803:GDFDEAKLAEAREMIRYMALVSAMERTEHKAKKKGTSALLSAKVTDMVMRKRRNTNYTQV  862
HSV2 811:GGFDEAKLAEAREMIRYMALVSAMERTEHKARKKGTSALLSSKVTNMVLRKRNKARYSPL  870

HSV1 863:PNKDGDAIEDDL                                                  874
HSV2 871:HNEDEAGDEDEL                                                  882
```

MODIFIED HSV GB PROTEIN AND HSV VACCINE INCLUDING SAME

RELATED PATENT APPLICATIONS

This application is based on and claims the benefit of priority from International Application No. PCT/JP2018/032020, filed on Aug. 29, 2018, which claims priority to Japanese Patent Application No. 2017-165684, filed on Aug. 30, 2017, the contents of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Feb. 21, 2020, is named "FP18-0825-00_Sequence_listing.txt" and is 25.3 KB in size.

TECHNICAL FIELD

The present invention relates to modified HSV gB proteins and HSV vaccines containing the same.

BACKGROUND ART

Herpes simplex virus (HSV) is a neurotropic pathogen, and transits to sensory nerves after initial infection into mucosal epithelium, then latently infects for a lifetime at trigeminal ganglion or sacral ganglion. Latent HSV sometimes reactivates, causing a variety of pathologies (Non Patent Literature 1).

Two serotypes (HSV-1, HSV-2) are known for HSV. HSV-1 predominantly causes lip/corneal herpes, and HSV-2 predominantly causes genital herpes. However, in recent years, due to the diversification of sexual activity or the like, HSV-1 sometimes causes genital herpes and HSV-2 sometimes causes lip herpes. The antibody-positive (pre-infected) ratio in Japan is 60-80% for HSV-1 and 10% for HSV-2, and the potential demand for vaccines is estimated to be 10 million people even for HSV-2 alone (Non Patent Literature 2). The antibody-positive (pre-infected) ratio in the United States is 57% for HSV-1 and 20% for HSV-2 (of which about 10% has suffered from manifest genital herpes) (Non Patent Literature 3).

Five envelope glycoproteins are known to be involved in the establishment of HSV infection into cells at two stages, adsorption and entry. These five envelope glycoproteins are each referred to as envelope glycoprotein B (gB), envelope glycoprotein C (gC), envelope glycoprotein D (gD), envelope glycoprotein H (gH), and envelope glycoprotein L (gL) (Non Patent Literature 4).

First, the adsorption process prompts gB and gC to bind to heparan sulfate on the cell surface (Non Patent Literatures 5 and 6). This process is not essential for HSV entry into the cells, but is believed to be involved in more efficient entry. Next, during the entry process, gB and gD bind to the respective host cell receptors and the entry is initiated by fusion of the viral envelope and the host cell membrane.

As host cell receptors, gB receptors and gD receptors are known. As the gB receptors, NM-IIA (Non Patent Literatures 7 and 8) and MAG (Non Patent Literature 9) have been identified. As the gD receptors, Nectin 1 (Non Patent Literature 10), HVEM (Non Patent Literature 11), and 3-O-sulfated heparan sulfate (Non Patent Literature 12) have been identified. It is also known that gH/gL heterodimers interact with gB and gD and play an important role in the membrane fusion (Non Patent Literature 13).

The elucidation of HSV-1 gB structure in 2006 revealed that gB forms a trimer having five domains (Non Patent Literature 14). In addition, gB takes a similar structure to gG of VSV (Vesicular stomatitis virus) known as a membrane fusion protein, which confirms that gB is a membrane fusion protein of HSV. Furthermore, gB is also highly conserved in other herpes viruses and its function is believed to be common to herpes viruses.

Pathogens causing an infection are roughly classified into Class I pathogen, which can be achieved sufficient efficacy with conventional vaccines, and Class II pathogen, which cannot be achieved sufficient protective immunity with conventional vaccines or pathogen infection history. As a reason for the difficulty to prevent Class II pathogen, the ingenious immunoediting system they have has been pointed out (Non Patent Literature 15). The HSV is classified as a Class II pathogen, which is believed that because the HSV has an immunoediting system and ingeniously passes through the host's immune reaction. Regarding the development of HSV vaccine, researches with a weakly toxic live vaccine or an adjuvant inactivated vaccine have been tried. However, either response is inadequate in both of T cell immune and B cell immune and did not differ significantly from the level of inadequate immune responses obtained after natural infection.

CITATION LIST

Non Patent Literature

Non Patent Literature 1: Roizman, B. et al., Herpes simplex viruses, p. 2501-2602. In D. M. Knipe and P. M. Howley (ed.), "Fields Virology", 5th ed. Lippincott Williams &Wilkins, Philadelphia, P.A. 2007

Non Patent Literature 2: Hashido M et al., An epidemiologic study of herpes simplex virus type 1 and 2 infection in Japan based on type-specific serological assays, Epidemiol Infect. 1998 March; 120 (2): 179-86

Non Patent Literature 3: Decision Resources; Emerging Vaccines 2008

Non Patent Literature 4: Viruses, 2010, Vol. 60, No. 2, pp. 187-196

Non Patent Literature 5: Herold, B. C. et al., Glycoprotein C-independent binding of herpes simplex virus to cells requires cell surface heparan sulphate and glycoprotein B. J Gen Virol 1994 75 (Pt 6):1211-22

Non Patent Literature 6: Herold, B. C. et al., Glycoprotein C of herpes simplex virus type 1 plays a principal role in the adsorption of virus to cells and in infectivity. J Virol 1991 65:1090-8

Non Patent Literature 7: Arii, J. et al., Non-muscle myosin IIA is a functional entry receptor for herpes simplex virus-1. Nature 2010 467:859-62

Non Patent Literature 8: Satoh, T. et al., PILRalpha is a herpes simplex virus-1 entry coreceptor that associates with glycoprotein B. Cell 2008 132:935-44

Non Patent Literature 9: Suenaga, T. et al., Myelin-associated glycoprotein mediates membrane fusion and entry of neurotropic herpesviruses. Proc Natl Acad Sci USA 2010 107:866-71

Non Patent Literature 10: Geraghty, R. J. et al., Entry of alphaherpesviruses mediated by poliovirus receptor-related protein 1 and poliovirus receptor. Science 1998 280:1618-20

Non Patent Literature 11: Montgomery, R. I. et al., Herpes simplex virus-1 entry into cells mediated by a novel member of the TNF/NGF receptor family. Cell (1996)87: 427-36

Non Patent Literature 12: Shukla, D., et al., A novel role for 3-O-sulfated heparan sulfate in herpes simplex virus 1 entry. Cell 1999 99:13-22

Non Patent Literature 13: Eisenberg R J et al., Herpes virus fusion and entry: a story with many characters. Viruses 2012 4:800-832 10.3390/v4050800

Non Patent Literature 14: SCIENCE 2006 313, 14, 217-220

Non Patent Literature 15: Vaccine 26 (2008) 6189-6199

Non Patent Literature 16: The Journal of Immunology, 1997, 159 279-289.

SUMMARY OF INVENTION

Technical Problem

As discussed above, antiviral drugs such as acyclovir have been used to treat HSV. However, these antiviral drugs cannot completely remove the virus, and the virus reactivates when taking of the drugs is stopped. Thus, while it is desirable to develop a preventive vaccine that prevents infection of HSV itself or a therapeutic vaccine that relieves symptoms of recurrence, currently there is no valid vaccine and its unmet needs are high.

An object of the present invention is to provide modified HSV gB proteins and vaccines containing the same that can induce, upon immune induction, antibodies containing a higher percentage of neutralizing antibodies that exhibit higher neutralizing activity against HSV gB compared to wild-type HSV gB and can be utilized for the prevention and/or treatment of HSV infections.

Solution to Problem

For gB proteins known as one of the major preventive antigens of HSV, the present inventors attempted to perform comprehensive B cell epitope analysis to classify beneficial epitopes (neutralizing epitopes) and unbeneficial or deleterious epitopes (non-neutralizing epitopes) in preventive activity expression. Then, by de-epitoping unbeneficial or deleterious epitopes and immunologically emphasizing beneficial epitopes, the present inventors have completed a modified HSV gB protein having enhanced neutralizing antibody-inducing ability and infection prevention ability, and a vaccine containing the modified HSV gB protein.

That is, the present invention relates to each of the following inventions.

(1) A modified protein of a herpes simplex virus (HSV) envelope glycoprotein B (gB) (modified HSV gB protein), wherein the modified HSV gB protein is derived from a wild-type HSV gB by modification of at least one of non-neutralizing antibody-inducing epitopes (non-neutralizing epitopes) present in domain IV and domain I of the wild-type HSV gB, so that the modified epitope does not function as an epitope.

(2) The modified HSV gB protein according to (1), wherein the non-neutralizing epitope is an epitope containing at least one amino acid residue present in a region at a distance 1.5 nm or less from an amino acid residue corresponding to an arginine residue at position 567 (R567), an arginine residue at position 602 (R602), a serine residue at position 631 (S631), or an aspartic acid residue at position 199 (D199) in an amino acid sequence set forth in SEQ ID NO: 1 in a surface of a crystal structure of an ectodomain of the wild-type HSV gB.

(3) The modified HSV gB protein according to (1) or (2), wherein the non-neutralizing epitope is an epitope containing an amino acid residue corresponding to R567, R602, 5631, or D199 in the amino acid sequence set forth in SEQ ID NO: 1.

(4) The modified HSV gB protein according to any one of (1) to (3), wherein the modification includes a modification performed by a substitution of an amino acid residue and/or a deficiency of an amino acid residue.

(5) The modified HSV gB protein according to (4), wherein the modification includes a modification performed by introducing a glycochain by the substitution or deficiency of an amino acid residue.

(6) The modified HSV gB protein according to any one of (1) to (5), wherein the modification includes a modification for introducing the glycochain to a position of at least one amino acid residue selected from the group consisting of amino acid residues corresponding to D199, R567, R602 and 5631 in the amino acid sequence set forth in SEQ ID NO: 1.

(7) The modified HSV gB protein according to any one of (1) to (6), wherein the modification includes a modification for introducing the glycochain to a position of at least two amino acid residues selected from the group consisting of amino acid residues corresponding to D199, R567, R602 and 5631 in the amino acid sequence set forth in SEQ ID NO: 1.

(8) The modified HSV gB protein according to (7), wherein the modification includes a modification for introducing the glycochain to each position of amino acid residues corresponding to R567 and 5631 in the amino acid sequence set forth in SEQ ID NO: 1.

(9) The modified HSV gB protein according to (8), wherein the modification includes a modification for introducing the glycochain to each position of amino acid residues corresponding to R567 and 5631 in the amino acid sequence set forth in SEQ ID NO: 1.

(10) The modified HSV gB protein according to (7), wherein the modification includes a modification for introducing the glycochain to each position of amino acid residues corresponding to D199, R567 and S631 in the amino acid sequence set forth in SEQ ID NO: 1.

(11) The modified HSV gB protein according to any one of (6) to (10), wherein the modification includes a modification for introducing the glycochain to a position of an amino acid residue corresponding to R602 in the amino acid sequence set forth in SEQ ID NO: 1.

(12) The modified HSV gB protein according to (11), wherein the introducing the glycochain is performed by amino acid residue substitutions of R602N, D603A, A604T in the amino acid sequence set forth in SEQ ID NO: 1.

(13) The modified HSV gB protein according to any one of (5) to (12), wherein the modification includes a modification for introducing the glycochain to a position of an amino acid residue corresponding to D199 in the amino acid sequence set forth in SEQ ID NO: 1.

(14) The modified HSV gB protein according to (13), wherein the introducing the glycochain is performed by amino acid residue substitutions of D199N, D200A, and H201T in the amino acid sequence set forth in SEQ ID NO: 1.

(15) The modified HSV gB protein according to any one of (4) to (14), wherein the modification includes a substitution of an amino acid residue corresponding to an arginine at position 613 (R613) in the amino acid sequence set forth in SEQ ID NO: 1 with an alanine residue.

(16) An HSV vaccine comprising the modified HSV gB protein according to any one of (1) to (15).

(17) A modified protein of a herpes simplex virus (HSV) envelope glycoprotein B (gB) (modified HSV gB protein), wherein at least one amino acid residue present in a region at a distance of 1.5 nm or less from an amino acid residue corresponding to an arginine residue at position 567 (R567), an arginine residue at position 602 (R602), a serine residue at position 631 (S631), or an aspartic acid residue at position 199 (D199) in an amino acid sequence set forth in SEQ ID NO: 1 in a surface of a crystal structure of an ectodomain of wild-type HSV gB is substituted or deleted.

(18) The modified HSV gB protein of (17), wherein the modification includes a modification for introducing a glycochain to a position of at least one amino acid residue selected from the group consisting of amino acid residues corresponding to D199, R567, R602 and 5631 in the amino acid sequence set forth in SEQ ID NO: 1.

(19) The modified HSV gB protein according to (17) or (18), wherein the modification includes a modification for introducing the glycochain to a position of an amino acid residue corresponding to D199 in the amino acid sequence set forth in SEQ ID NO: 1.

(20) The modified HSV gB protein according to any one of (17) to (19), wherein the modification includes a substitution of an amino acid residue corresponding to an arginine at position 613 (R613) in the amino acid sequence set forth in SEQ ID NO: 1 with an alanine residue.

(21) The modified HSV gB protein according to any one of (17) to (20), wherein the modification includes a modification for introducing the glycochain to a position of an amino acid residue corresponding to R567 in the amino acid sequence set forth in SEQ ID NO: 1.

(22) The modified HSV gB protein according to any one of (17) to (21), wherein the modification includes a modification for introducing the glycochain to a position of an amino acid residue corresponding to S631 in the amino acid sequence set forth in SEQ ID NO: 1.

(23) An HSV vaccine comprising the modified HSV gB protein according to any one of (18) to (22).

Advantageous Effects of Invention

When immunity is induced by modified HSV gB proteins of the present invention and vaccines comprising the same, relatively more neutralizing antibodies with higher neutralizing activity can be contained in serum as compared to when immunity is induced by wild-type HSV gB. That is, the modified HSV gB proteins of the present invention and vaccines containing the same can induce immune refocusing and provide a strong protective effect against HSV. Thus, high preventive and therapeutic effects can be expected against HSV infections.

BRIEF DESCRIPTION OF DRAWINGS

FIG. 10 is a diagram showing the result of survival rate of the mouse infection-prevention test of bcev50 in Example 5.

FIG. 11 is a diagram showing the result of symptom score of the mouse infection-prevention test of bcev50 in Example 5.

FIG. 15 is a diagram showing the comparison result of bcev19 and bcev19' in the mouse immunogenicity test of Example 5.

FIG. 17 is a diagram showing the comparison result of multiple alignments of the amino acid sequence of HSV-1 derived gB (SEQ ID NO: 2) and the amino acid sequence of HSV-2 derived gB (SEQ ID NO: 3). The italics indicate the leader sequence, and the underlines indicate the amino acid residues at positions 383 to 388 (I383-R388) of HSV-1 derived gB domain II and the amino acid residues at positions 386 to 391 (I386-R391) of HSV-2 derived gB domain II.

DESCRIPTION OF EMBODIMENTS

Figure 1:
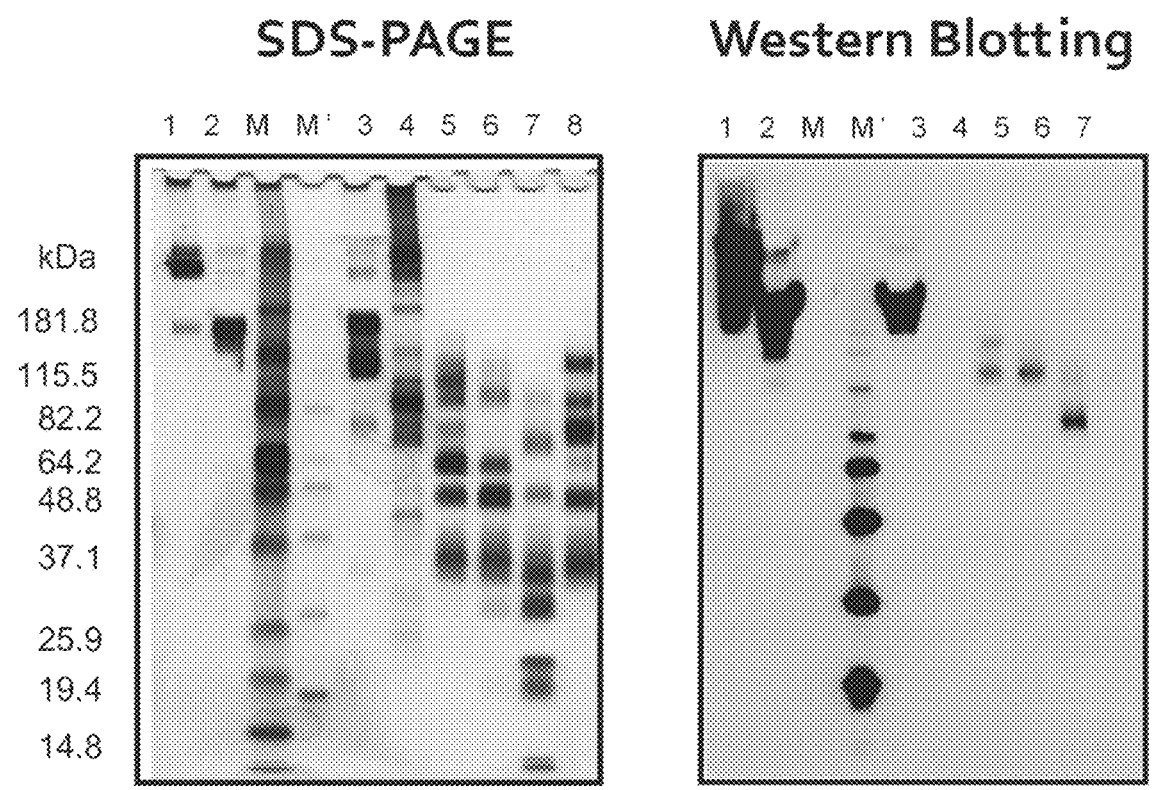
FIG. 1 is a diagram showing the results of SDS-PAGE and Western Blotting using gB of Example 2 and protease cleavage fragments thereof.

Hereinafter, the embodiments for carrying out the present invention are described in detail below. However, the present invention is not limited to the following embodiments.

The modified HSV gB protein of the present invention is a modified protein of an envelope glycoprotein B (gB) of herpes simplex virus (HSV), which is modified so that at least one non-neutralizing antibody-inducing epitope (non-neutralizing epitope) present in domains IV and I of wild-type gB, does not function as an epitope.

The present invention is based on the hypothesis proposed by the present inventors that there is a "decoy region" in the HSV gB antigen. The "decoy region" is derived from an English word "Decoy" and is considered one of the immunoediting systems by which the pathogen escapes the host's immune response. The "decoy region" is an antigen region that induces antibodies having no or low neutralizing antibody activity, and is believed to be a mechanism by which pathogens escape the host's immune response such that the neutralizing antibodies are not produced or are produced in small amounts by the deceptive inprinting (also referred to as "immune deviation").

Until now, the presence of the decoy region has not been confirmed in HSV, not even the concept of the decoy region.

The present inventors performed detailed epitope mapping analyses on anti-gB monoclonal antibodies obtained by comprehensive exploration of anti-HSV gB antibodies performed using a human antibody library. As the result, domains IV and I of HSV gB were first revealed to be decoy regions in which unbeneficial or deleterious epitopes are concentrated. Furthermore, in these decoy regions, by de-epitoping the non-neutralizing epitopes and immunologically emphasizing the beneficial epitope, modified HSV gB proteins that are capable of inducing antibodies with high neutralizing activity have been finally obtained.

The "wild-type HSV gB" refers to the full length of HSV-1 derived envelope glycoprotein B (gB) having the amino acid sequence set forth in SEQ ID NO: 2, or HSV-2 derived gB having the amino acid sequence set forth in SEQ ID NO: 3. As the result of comparing the two sequences in multiple alignments, the sequence identity is about 87% (FIG. 17). The conformation of gB has also been analyzed and is known to consist of an intracellular domain, a transmembrane domain, and an ectodomain. The crystal structure of gB derived from HSV-1 has been reported, for example, by Science 313: 217-220 (2006) and J. Virol. 84: 12924-12933 (2010). Although the crystal structure of gB derived from HSV-2 has not been reported, it can be analyzed similarly according to the crystallization method of gB derived from HSV-1 described above. The "ectodomain of wild-type HSV gB" means a soluble, antigenic extracellular region of the wild-type HSV gB. An example of the ectodomain of the wild-type HSV gB is a wild-type gB ectodomain 1-705 derived from a 333 strain of HSV-2 consisting of the amino acid sequence set forth in SEQ ID NO: 1.

In the crystal structure of gB, domains IV and I, located at the top (Crown) and bottom (Bottom) respectively, are "more conspicuous" than domain II located at the middle (Middle), resulting in higher antigen presentation. Indeed in antibodies in blood, as investigated by the present inventors, the percentage of antibodies to domains IV and I is higher, and the percentage of antibodies to domain II is lower. However, according to the investigation by the present inventors, whereas domain II of wild-type HSV gB only contains an epitope that induce a neutralizing antibody (herein referred to as a "neutralizing epitope"), domains IV and I of wild-type HSV gB contain not only neutralizing epitopes but also an epitope that induces a non-neutralizing antibody (herein referred to as a "non-neutralizing epitope"). Since non-neutralizing antibodies bind antigens (i.e., viruses) but are unable to suppress the viral activity, it is believed that ability to induce production of neutralizing antibodies rather than non-neutralizing antibodies is important, particularly in the manufacture of vaccines.

The modified HSV gB proteins of the present invention can derive antibodies having high neutralizing activity by "de-epitoping" the "conspicuous" domains IV and I, which are less beneficial for the production of neutralizing antibodies, and making them "inconspicuous", thereby making the domain II containing neutralizing epitopes "conspicuous".

The "modified HSV gB protein" ("modified protein of HSV gB" or "variant") is a protein in which at least one amino acid residue or a region of contiguous amino acid residues is substituted, deleted or added to a wild-type HSV gB, and includes a protein in which a protein modification that is not present in the wild-type is performed, such as a protein in which a glycochain is introduced by substitution or deficiency of the amino acid residue. The modified HSV gB protein of the invention has higher neutralizing antibody-inducing activity than the wild-type protein.

The "neutralizing antibody-inducing activity" refers to the ability to induce neutralizing antibodies of an antigen protein, and can be evaluated by the neutralizing antibody titer in immune serum obtained by inoculating the antigen protein in a subject animal. The "neutralizing antibody" refers to an antibody that is capable of losing the infectivity of a viral particle. The neutralizing antibody is, for example, evaluated by the intensity of neutralizing activity of the antibody at a concentration (NT50) necessary to reduce the plaque number of the subject virus by 50%.

The "de-epitoping" refers to a modification of a site contributed to antibody production as an epitope in the wild-type HSV gB so as not to function as an epitope. Examples of the method of de-epitoping include a method of substituting an amino acid residue at the site of an epitope with another amino acid residue; a method of defecting (deleting) an amino acid residue at the site of an epitope; and a method of introducing a glycochain by substitution or deficiency of an amino acid residue at the site of an epitope. As the method of de-epitoping, the method of introducing a glycochain, in particular an N-type glycochain (N-glycoside-linked glycochain) is preferable. The method has advantages in that not only the portion where the glycochain is introduced, but also the epitopes in the periphery can be masked at the same time due to its bulkiness. Considering the size ratio to proteins such as antibodies or receptors that interact with gB, it is expected that the dot-to-dot interaction such that binding is formed in a very narrow range of about a few amino acids is less likely to occur. In the binding between gB and receptors, it is believed that a network of facet-to-facet interaction is formed such that a wide range of amino acids cooperate to form a binding. Introduction of a glycochain is believed to be an effective way of de-epitoping to hide peripheral residues extensively by its own bulkiness, and simultaneously to inhibit access of the binding partner. It is also reported that the glycochain is difficult to induce anti-glycochain antibodies, thus it is believed that the likelihood of new immunogenicity due to modification can be reduced.

An example of the non-neutralizing antibody-inducing epitope (non-neutralizing epitope) present in domains IV and I of wild-type HSV gB includes an epitope containing at least one amino acid residue present in a region at a distance of 1.5 nm or less from an amino acid residue corresponding to an arginine residue at position 567 (R567), an arginine residue at position 602 (R602), a serine residue at position 631 (S631) or an aspartic acid residue at position 199 (D199), more preferably a region at a distance of 1 nm or less from the amino acid residue, in the amino acid sequence set forth in SEQ ID NO: 1 in a surface of a crystal structure of an ectodomain of the wild-type HSV gB. Here, the "distance from an amino acid residue" refers to the linear distance from the amino acid residue described above, regardless of the shape of the surface of the crystal structure of the wild-type HSV gB ectodomain. Since non-neutralizing epitopes induce the production of unbeneficial or deleterious antibodies and are not beneficial for the production of neutralizing antigens, de-epitoping of these non-neutralizing epitopes can reduce the production of unbeneficial or deleterious antibodies and increase the production of neutralizing antibodies by emphasizing beneficial epitopes. The crystallization methods are not particularly limited, but examples thereof include a crystallization method described in J. Virol. 84: 12924-12933 (2010). For example, crystals of gB can be grown with 15% PEG 4000-0.3 M NaCl-0.1 M sodium citrate, pH 5.5.

Examples of the non-neutralizing epitope include epitopes containing an amino acid residue corresponding to an arginine residue at position 567 (R567), an arginine residue at position 602 (R602), a serine residue at position 631 (S631) or an aspartic acid residue at position 199 (D199) in the amino acid sequence set forth in SEQ ID NO: 1. Since these epitopes have been proven to be non-neutralizing epitopes by the present inventors, de-epitoping of these epitopes can reduce the production of unbeneficial or deleterious antibodies in preventive activity expression. Furthermore, de-epitoping of these epitopes can also increase the percentage of production of neutralizing antibodies by emphasizing beneficial epitopes.

The modification for de-epitoping include a modification performed by introducing a glycochain by a substitution of an amino acid residue, a deficiency of an amino acid residue, and/or a substitution or deficiency of an amino acid residue.

It is preferred that the modification includes a modification for introducing the glycochain to a position of at least one amino acid residue, preferably at least two amino acid residues, selected from the group consisting of amino acid residues corresponding to an aspartic acid residue at position 199 (D199), an arginine residue at position 567 (R567), an arginine residue at position 602 (R602), and a serine residue at position 631 (S631) in the amino acid sequence set forth in SEQ ID NO: 1. It is preferred that the modification includes a modification for introducing a glycochain to each position of amino acid residues corresponding to R567 and S631 in the amino acid sequence set forth in SEQ ID NO: 1, and it is preferred that the introducing a glycochain is performed by amino acid residue substitutions of R567N, P568S, G569S, S631N, H632T and Q633T in the amino acid sequence set forth in SEQ ID NO: 1. It is further preferred that the modification includes a modification for introducing a glycochain to each position of amino acid residues corresponding to D199, R567 and S631 in the amino acid sequence set forth in SEQ ID NO: 1. It is preferred that the modification further includes a modification for introducing a glycochain to a position of an amino acid residue corresponding to R602 in the amino acid sequence set forth in SEQ ID NO: 1, and it is preferred that the introducing a glycochain is performed by amino acid residue substitutions of R602N, D603A, A604T in the amino acid sequence set forth in SEQ ID NO: 1. It is preferred that the modification further includes a modification for introducing a glycochain to a position of an amino acid residue corresponding to D199 in the amino acid sequence set forth in SEQ ID NO: 1, and it is preferred that the introducing a glycochain is performed by amino acid residue substitutions of D199N, D200A and H201T in the amino acid sequence set forth in SEQ ID NO: 1.

The method of introducing a glycochain is not particularly limited as long as it is a conventional method. For example, when an N-type glycochain is introduced, a cDNA of wild-type gB protein (GenBank: M15118.1, SEQ ID NO: 4) is used as a template, and the primer is designed such that the three continuous amino acid sequences of the site of interest at which the N-type glycochain is introduced become N-X-S/T (X is any amino acid other than proline), then a mutation is introduced by PCR. Examples of the mutations for introducing a glycochain include the following mutations in the amino acid sequence set forth in SEQ ID NO: 1: (D199N, D200A, H201T), (R567N, P568S, G569S), (S631N, H632A, Q633T), and (S631N, H632T, Q633T).

The nucleic acid sequence of the modified gB protein of interest, or the nucleic acid sequence further linked to a tag such as 6×His as required, can be cloned into an appropriate vector, then expressed to acquire a gB variant. Then, an N-type glycochain is added to asparagine at the site of interest of the gB variant by a conventional method.

The modification of the non-neutralizing epitope may further include a substitution of a charged amino acid residue that is an epitope, with a non-characteristic amino acid residue, e.g., an alanine residue. This method, unlike the introduction of an N-type glycochain, has an advantage that it can achieve de-epitoping by pinpoint. For example, it is preferred that the alanine substitution includes a substitution of an amino acid residue corresponding to an arginine at position 613 (R613) in the amino acid sequence set forth in SEQ ID NO: 1 with alanine.

It is preferred that the modified HSV gB protein is a gB protein in which a glycochain is introduced into each of the amino acid residues corresponding to D199, R567 and S631 in the amino acid sequence set forth in SEQ ID NO: 1, and the amino acid residue corresponding to an arginine at position 613 (R613) in the amino acid sequence set forth in SEQ ID NO: 1 is substituted with alanine. As another example, it is further preferred that the modified HSV gB protein is a gB protein in which a glycochain is introduced into each of the amino acid residues corresponding to D199, R567, R602 and S631 in the amino acid sequence set forth in SEQ ID NO: 1, and the amino acid residue corresponding to an arginine at position 613 (R613) in the amino acid sequence set forth in SEQ ID NO: 1 is substituted with alanine.

The modified HSV gB protein of the present invention can be produced by genetic engineering methods. Production methods thereof are not particularly limited, but examples thereof include a production method including: using the cDNA of the wild-type gB protein as a template; designing a primer to introduce the mutation of interest; obtaining a nucleic acid into which the mutation has been introduced by PCR; functionally linking the nucleic acid to an expression promoter, and optionally a tag; and introducing the resultant into an appropriate expression vector to express a modified HSV gB protein. Alternatively, the modified HSV gB protein by introducing a glycochain can be obtained as described above.

The produced modified HSV gB protein may be purified as needed. Purification methods are not particularly limited, but examples thereof include purifications with affinity chromatography column.

HSV infections include infections by HSV-1 and HSV-2, and examples thereof include lip herpes, corneal herpes, genital herpes, systemic neonatal herpes, and stomatitis, skin diseases, encephalitis, meningitis and myelitis due to HSV.

The HSV vaccine of the present invention contains the modified HSV gB protein of the present invention.

Examples of the dosage form of the HSV vaccine of the present embodiment include, liquid, powder (lyophilized powder, dried powder), capsule, tablet, and frozen form.

The HSV vaccine of the present embodiment may contain a pharmaceutically acceptable carrier. As the carrier, carriers commonly used in vaccine production can be used without limitation, and specific examples thereof include saline, buffered saline, dextrose, water, glycerol, isotonic aqueous buffers, and combinations of these. The vaccine may further contain emulsifiers, preservatives (e.g., thimerosal), isotonic agents, pH adjusting agents, and the like.

It is also possible that the HSV vaccine of the present embodiment further contains an adjuvant to further enhance the immunogenicity. Examples of the adjuvant include aluminum adjuvants; oil-in-water emulsion adjuvants containing squalene (AS03, MF59, or the like), ligands of Toll-like receptors such as CpG and 3-O-deacylated-4'-monophosphoryl lipid A (MPL); saponin-based adjuvants; polymer-based adjuvants such as polyγ-glutamic acid; and polysaccharides such as chitosan and inulin.

The HSV vaccine of the present embodiment can be obtained by mixing a modified HSV gB protein of the present invention with a carrier, adjuvant, or the like, as needed. The adjuvant may be mixed when used.

Examples of the administration route of the HSV vaccine of the present embodiment include transdermal administration, sublingual administration, ophthalmic administration, intradermal administration, intramuscular administration, oral administration, enteral administration, nasal administration, intravenous administration, subcutaneous administration, intraperitoneal administration, and oral to pulmonary inhalation administration.

Examples of the administration method of the HSV vaccine of the present embodiment include a syringe, a transdermal patch, a microneedle, an implantable sustained-release device, a syringe with microneedle, a needleless device, and a spray.

EXAMPLES

Hereinafter, the present invention is described in more detail based on examples. However, the present invention is not limited to the following examples.

Example 1 Isolation of Anti-gB Antibodies

The cDNA (SEQ ID NO: 4) of gB ectodomain 1-705aa (gB1-705) derived from a wild-type HSV-2 333 strain was cloned into pCAGGS1-dhfr-neo. The gB was designed so that StrepTag II was added to the C-terminal. For expression, a FreeStyle 293 or Expi293 expression system (Life Technologies) was used. Expression plasmids were transfected into cells and culture supernatants were collected at 4-6 days. The culture supernatants containing gB were concentrated with UF membranes to remove biotin contained in the medium. The concentrated culture supernatant was purified with a StrepTactin column to acquire purified gB2. The gene encoding amino acids from 370 to 457aa of gB were amplified by PCR and cloned into pET43.1b(+) to construct a gB370-457 expression plasmid. To facilitate purification, a Nus-Tag gene and a His-Tag gene were added to this plasmid. The plasmid was transformed into Rosetta2 (Novagen). After culturing the transformant in LB medium at 37° C. until the mid-log growth period, expression was induced with 1 mM IPTG and culturing was performed at 25° C. overnight. For the extraction of soluble proteins, BugBuster mix was used. The obtained protein was purified with Ni NTA Agarose (QIAGEN).

The scFv-phage display library prepared using human VH and VL cDNAs from human B cell-derived mRNA from tonsils and spleens was screened to isolate 44 scFv clones having reactivity with HSV-2 gB. The DNA nucleotide sequences of the VH and VL chain genes of the isolated scFv gene were determined with Big Dye Terminator v3.1 Cycle Sequencing Kit (Applied Biosystems). Each clone had an independent sequence and was expected to have variations in its epitopes. Multiple scFv clones, except for 44 clones, were obtained, but most of which had sequences similar to D1 or D2 (data not shown). D1 and D2 are the VH5 family and their antibody populations in organisms are small.

Example 2 Classification of Anti-gB Antibodies

<Preparation of Antibody Fragment scFv-hFc>

The variable region of the isolated scFv gene was linked to human Fc gene, and cloned into a pCAG vector to construct a scFv-hFc expression plasmid. For expression, a FreeStyle 293 or Expi 293 expression system was used. Expression plasmids were transfected into cells and culture supernatant was collected at 4-6 days. From the culture supernatant, scFv-hFc was purified using Ab Rapid Pure 10 (ProteNova Co., Ltd). Furthermore, *E. coli* TG1 strains with phagemid vectors in which each scFv gene was cloned were cultured in 2×YTCG medium (37° C.). After M13K07 helper phage was infected with moi=20, phage expression was performed in 2×YTCK medium (25° C.) overnight. The obtained scFv-phages were concentrated with 20%-PEG-2.5M NaCl.

The binding activities of the acquired scFv-phage and scFv-hFc were evaluated by ELISA. The gB1-705 was diluted with PBS to 1 μg/mL, then 50 μL of the dilution was placed in Maxisorp plate (Nunc) and incubated at 4° C. overnight or at room temperature for 1-2 hours to make the recombinant gB immobilized. After the immobilization, the plate was washed with PBS, and 100 μL of the acquired scFv-phage, IgG was added to wells of the plate and incubated at 37° C. After 1 hour, the plate was washed with PBST, and 100 μL of the detection antibody anti-M13/HRP (GE Healthcare) or anti-hFc/HRP (Cosmo Bio Co., Ltd.) was added to the wells of the plate and incubated at 37° C. After 1 hour, the plate was washed with PBST and colored by adding 100 μL of TMB to the wells of the plate. After 30 minutes, the reaction was stopped with 1N sulfuric acid, and absorbance (O.D. 450 nm/650 nm) was measured with a microplate reader (Molecular Devices, LLC.) (data not shown).

<Classification of Anti-gB Antibodies by Western Blotting Using gB and its Protease Cleavage Fragments>

To perform grouping of the obtained 44 anti-gB antibody clones, western blotting was performed using gB fragments obtained by digesting gB1-705 with trypsin or chymotrypsin, gB1-705 and cleavage variants thereof as materials.

500 ng of denatured or non-denatured gB1-705 was loaded to 8-16% SDS-PAGE and electrophoresed. The denatured gB1-705 was obtained by adding 2% 2-mercaptoethanol to gB1-705 and boiling the mixture at 96° C. for 5 minutes. The non-denatured gB1-705 did not undergo these procedures and was directly loaded. The gB fragments digested with trypsin or chymotrypsin were obtained as follows. To 0.5 M Tris-HCl (pH 8.0), 500 ng of gB1-705 and 1 ng, 5 ng or 1000 ng of trypsin, or 1 ng of chymotrypsin were added, and the mixture was stood still at 37° C. for 1 hour or 3 hours to be treated enzymatically, and SDS-PAGE loading buffer with 2% 2-mercaptoethanol (FUJIFILM Wako Pure Chemical Corporation) was added and the mixture was boiled at 96° C. for 5 minutes to stop the reaction. Each sample was loaded to 8-16% SDS-PAGE and electrophoresed, the gel was transferred to a nitrocellulose membrane (Millipore) and blocked with 2% fat-free milk/PBS-T. After washed with PBS-T, the membrane was reacted with each scFv-hFc at a concentration of 1 μg/mL 2% fat-free milk-PBS-T at room temperature for 30 minutes. After washed again, the membrane was reacted with anti-hFc/HRP in 2% fat-free milk-PBS-T, and colored with Immobilon Western Detection Regent (Millipore). Silver staining was performed to detect SDS-PAGE bands.

The result is shown in FIG. 1. Samples for each lane of SDS-PAGE and Western Blotting in FIG. 1 are as follows. In SDS-PAGE, lane 1: non-reduced, non-denatured gB1-705; lane 2: boiled only gB1-705; lane 3: gB1-705 boiled and denatured with a denaturing agent; lane 4: gB370-457 boiled and denatured with a denaturing agent; lane 5: gB1-705 treated with 1 ng (1:500) of trypsin at 37° C. for 1 hour, boiled and denatured with a denaturing agent; lane 6: gB1-705 treated with 5 ng (1:100) of trypsin at 37° C. for 3 hours; lane 7: gB1-705 treated with 100 ng (1:5) of trypsin at 37° C. for 3 hours, boiled and denatured with a denaturing agent; lane 8: gB1-705 treated with 1 ng (1:500) of chymotrypsin at 37° C. for 1 hour, boiled and denatured with denaturing agent; lane M: BenchMark prestained Ladder; and lane M': Magic Western standard.

In analysis of non-reduced, non-boiled gB1-705 with SDS-PAGE, a band near about 300 kDa was detected (lane 1). Meanwhile, a band of boiled gB1-705 was detected near about 100 kDa (lane 2). This refers to trimers and monomers of gB, respectively, suggesting that the trimer is not formed via S—S bond because boiling changed trimers into monomers.

Treatments with trypsin or chymotrypsin respectively gave fragmented gBs. The reactivity of these gBs with antibody E7 scFv-hFc was detected by Western blotting. E7 scFv-hFc showed reactivity with non-reduced, non-boiled gB1-705 (lane 1), boiled gB1-705 (lane 2), reduced, boiled gB1-705 (lane 3), and protease-treated gB fragments (lanes 5, 6, 7) (FIG. 1). Similar reaction patterns were observed in antibodies E17 and E31 (Table 1). These suggest that antibodies E7, E17 and E31 scFv-hFc are continuous epitopes. Antibodies A17, D1, D2, D3, D37, D48, and E15 scFv-hFc showed reactivity with non-reduced, non-boiled gB1-705, boiled gB1-705, reduced, boiled gB1-705, and protease-treated gB fragments, although their reactivity with gB fragments showed a different pattern from those of E7, E17, E31 (Table 1). The reaction pattern between D1 and D2 was the same, and the reaction pattern between D3 and D37 was the same, suggesting that they recognize the same or proximal epitope, respectively.

The reactivity pattern of gB fragments were able to be classified into six groups. E41, F13, F18, F19, F22, F30 and F78 scFv-hFc showed reactivity only with non-reduced, non-boiled gB1-705 (Table 1). These antibody clones are trimeric-specific, suggesting that they are discontinuous epitopes. F7, F11, F12, F33, F52, F65, F67, F68, F69, F76, F80, F87, G39, G64, G76, H15, H34, H57, H61, H65, G10, G25 and G65 showed reactivity with boiled gB1-705 as well as non-reduced, non-boiled gB1-705 (Table 1). It is suggested that these antibody clones are not trimeric-specific, but discontinuous epitopes recognizing confirmation to some extent. E8, E35, E82, and E88 showed reactivity with non-reduced, non-boiled gB1-705, boiled gB1-705, and reduced boiled gB1-705, but their reactivity with cleavage fragments by proteases could not be confirmed (Table 1). It is suggested that these antibody clones are continuous epitopes because they were reactive with completely denatured gB, but the region may be susceptible to proteases. With analysis by Western blotting using the above gB and gB fragments, it was revealed that the acquired 44 anti-gB antibody clones are classified into nine groups. Of these, it was suggested that 30 clones are discontinuous epitopes and 14 clones are continuous epitopes.

TABLE 1

Reaction patterns of gB1-705 and its fragments with anti-gB antibodies

| Clone | 2ME-boil- ※1 | 2ME-boil+ ※1 | 2ME+boil+ ※1 | Fragment pattern A ※1 | Fragment pattern B ※1 | Fragment pattern C ※1 | Fragment pattern D ※1 | Fragment pattern E ※1 | Fragment pattern F ※1 |
|---|---|---|---|---|---|---|---|---|---|
| | | | | Protease-treatment ※2 | | | | | |
| A17 | + | + | + | + | − | − | − | − | − |
| D1 | + | + | + | − | + | − | − | − | − |
| D2 | + | + | + | − | + | − | − | − | − |
| D3 | + | + | + | − | − | + | − | − | − |
| D37 | + | + | + | − | − | + | − | − | − |
| D48 | + | + | + | − | − | − | + | − | − |
| E7 | + | + | + | − | − | − | − | + | − |
| E8 | + | + | + | − | − | − | − | − | − |
| E15 | + | + | + | − | − | − | − | − | + |
| E17 | + | + | + | − | − | − | − | + | − |
| E31 | + | + | + | − | − | − | − | + | − |
| E35 | + | + | + | − | − | − | − | − | − |
| E41 | + | − | − | − | − | − | − | − | − |
| E82 | + | + | + | − | − | − | − | − | − |
| E88 | + | + | + | − | − | − | − | − | − |
| F7 | + | + | − | − | − | − | − | − | − |
| F11 | + | + | − | − | − | − | − | − | − |
| F12 | + | + | − | − | − | − | − | − | − |
| F13 | + | − | − | − | − | − | − | − | − |
| F18 | + | − | − | − | − | − | − | − | − |
| F19 | + | − | − | − | − | − | − | − | − |
| F22 | + | − | − | − | − | − | − | − | − |
| F30 | + | − | − | − | − | − | − | − | − |
| F33 | + | + | − | − | − | − | − | − | − |
| F52 | + | + | − | − | − | − | − | − | − |
| F65 | + | + | − | − | − | − | − | − | − |
| F67 | + | + | − | − | − | − | − | − | − |
| F68 | + | + | − | − | − | − | − | − | − |
| F69 | + | + | − | − | − | − | − | − | − |
| F76 | + | + | − | − | − | − | − | − | − |

TABLE 1-continued

Reaction patterns of gB1-705 and its fragments with anti-gB antibodies

| Clone | 2ME−<br>boil−<br>※1 | 2ME−<br>boil+<br>※1 | 2ME+<br>boil+<br>※1 | Fragment<br>pattern A<br>※1 | Fragment<br>pattern B<br>※1 | Fragment<br>pattern C<br>※1 | Fragment<br>pattern D<br>※1 | Fragment<br>pattern E<br>※1 | Fragment<br>pattern F<br>※1 |
|---|---|---|---|---|---|---|---|---|---|
| | | | | Protease-treatment ※2 | | | | | |
| F78 | + | − | − | − | − | − | − | − | − |
| F80 | + | + | − | − | − | − | − | − | − |
| F87 | + | + | − | − | − | − | − | − | − |
| G10 | + | + | − | − | − | − | − | − | − |
| G25 | + | + | − | − | − | − | − | − | − |
| G39 | + | + | − | − | − | − | − | − | − |
| G64 | + | + | − | − | − | − | − | − | − |
| G65 | + | + | − | − | − | − | − | − | − |
| G76 | + | + | − | − | − | − | − | − | − |
| H15 | + | + | − | − | − | − | − | − | − |
| H34 | + | + | − | − | − | − | − | − | − |
| H57 | + | + | − | − | − | − | − | − | − |
| H61 | + | + | − | − | − | − | − | − | − |
| H65 | + | + | − | − | − | − | − | − | − |

※1 +: with reactivity, −: without reactivity, 2ME+: 2 mercaptoethanol-treated, boil+: boiled
※2 Protease-treatment was performed with trypsin and chymotrypsin. Reactivity patterns of gB fragments with antibodies were classified into six patterns A, B, C, D, E and F.

<Classification of Acquired Antibodies by Competitive ELISA>

To further perform grouping of the acquired 44 antibody clones, competitive ELISA using scFv-phage and scFv-hFc of each anti-gB clone was performed.

Competition between the acquired scFv-phage and scFv-hFc was evaluated by ELISA. The gB1-705 was diluted with PBS to 1 µg/mL, then 50 µL of the dilution was placed in Maxisorp Plate, and incubated at 4° C. overnight to make gB1-705 immobilized. After the immobilization, the plate was washed with PBS, and 50 µL of the acquired scFv-hFc was added to the wells of the plate and incubated at 25° C. After 1 hour, 50 µL of scFv-phage was added to the wells of the plate and incubated at 25° C. After 1 hour, the plate was washed with PBST, and 100 µL of the detection antibody anti-M13/HRP was added to the wells of the plate and incubated at 25° C. After 1 hour, the plate was washed with PBST and colored by adding 100 µL of TMB to the wells of the plate. After 30 minutes, the reaction was stopped with 1N sulfuric acid, and absorbance (O.D. 450 nm/650 nm) was measured with a microplate reader.

Figure 2:
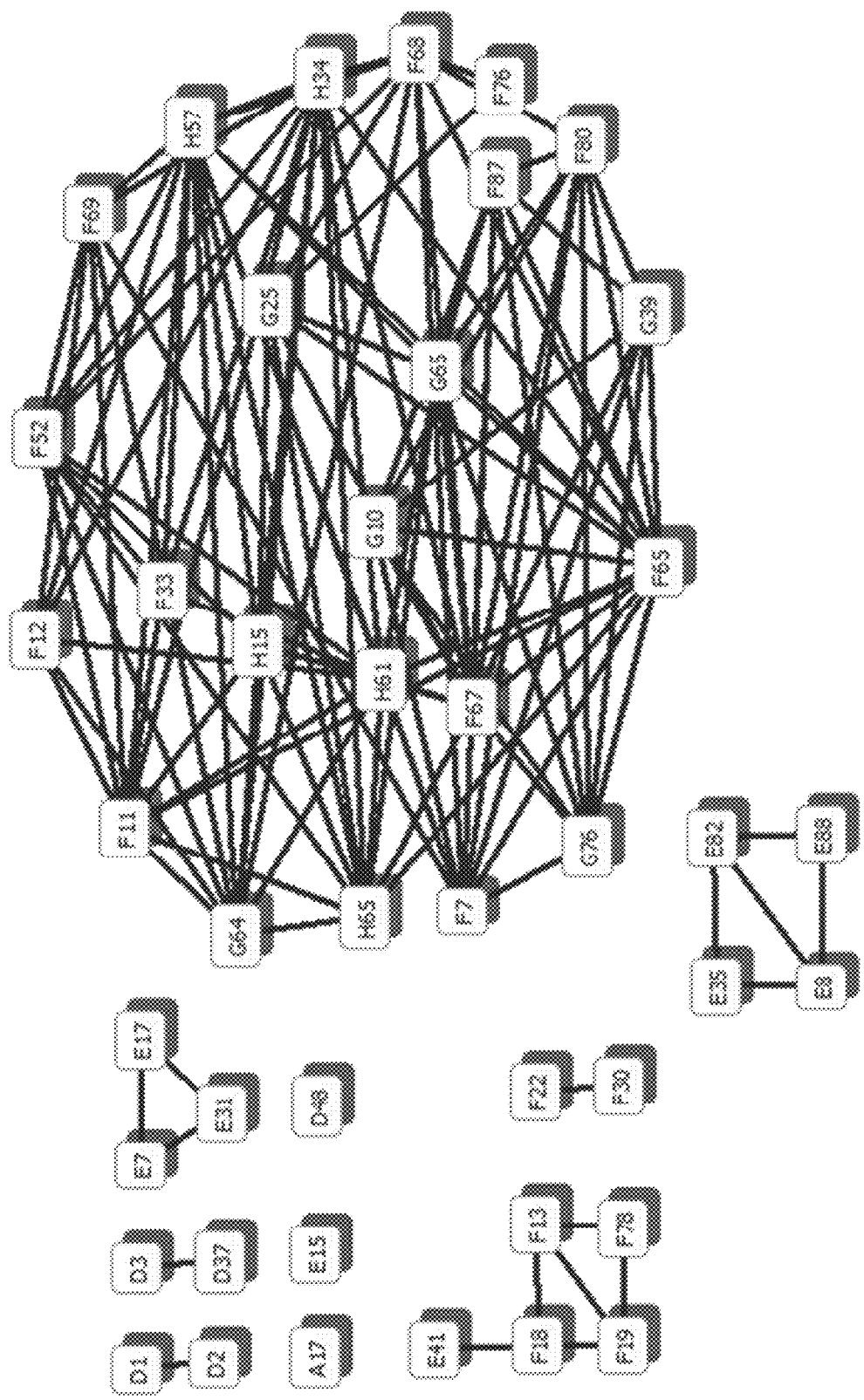
FIG. 2 is a correlation diagram obtained by classifying anti-gB antibodies obtained by competitive ELISA of Example 2.

Based on the results, a correlation diagram of the antibodies was made (FIG. 2). The group including antibodies E41, F18, F19, F13, F78, F22 and F30 was a group showing reactivity only with non-reduced, non-boiled gB1-705, but unlike other groups, it was confirmed that this group was classified into a group of antibodies E41, F18, F19, F13 and F78 and a group of F22 and F30, based on the results of competitive ELISA. Meanwhile, the other groups were not further subdivided from the groups described above. Thus, anti-gB clones were classified into a total of 10 groups. It was also suggested that an epitope is present within 370aa to 457aa of gB because D48 was reactive with gB370-457.

Example 3 Identification of Epitopes of gB Antibodies by Alanine Scanning

The genes in which each charged amino acid residue (187 locations) in the ectodomain of gB, 1-705aa, was modified with alanine were constructed by PCR and cloned into pCAGGS1-dhfr-neo. For expression, a FreeStyle 293 or Expi 293 expression system was used. The expression level of the acquired gB alanine substitute and the binding activity of the alanine substitute to the antibody fragment were evaluated by ELISA.

The culture supernatant containing the gB alanine substitute was placed in a Maxisorp plate and incubated at room temperature for 1 hour to make the gB alanine substitute immobilized. After the immobilization, the plate was washed with PBST, and 100 µL of the detection antibody StrepTactin/HRP (IBA) was added to wells of the plate and incubated at room temperature. After 1 hour, the plate was washed with PBST and colored by adding 100 µL of TMB to the wells of the plate. After 30 minutes, the reaction was stopped with 1N sulfuric acid, and absorbance (O.D. 450 nm/650 nm) was measured with a microplate reader to determine expression level.

Meanwhile, the culture supernatant containing the gB alanine substitute was placed in a Streptactin-immobilized Maxisorp plate and incubated at room temperature for 1 hour to make the gB alanine substitute immobilized. After the immobilization, the plate was washed with PBST and 100 µL of antibody fragments were added to wells of the plate and incubated at room temperature. After 1 hour, the plate was washed with PBST, and 100 µL of the detection antibody anti-human Fc/HRP (Cosmo Bio Co., Ltd.) was added to the wells of the plate and incubated at room temperature. After 1 hour, the plate was washed with PBST and colored by adding 100 µL of TMB to the wells of the plate. After 30 minutes, the reaction was stopped with 1N sulfuric acid, color value (O.D. 450 nm/650 nm) was measured with a microplate reader to determine binding activity. Epitope candidates were selected based on whether the reactivity per expression level was changed compared to that of wild-type gB1-705, non-alanine substitute. In addition, in the case of antibodies requiring scrutiny, epitope candidates were narrowed down by ELISA using purified gB alanine substitutes.

Figure 3:
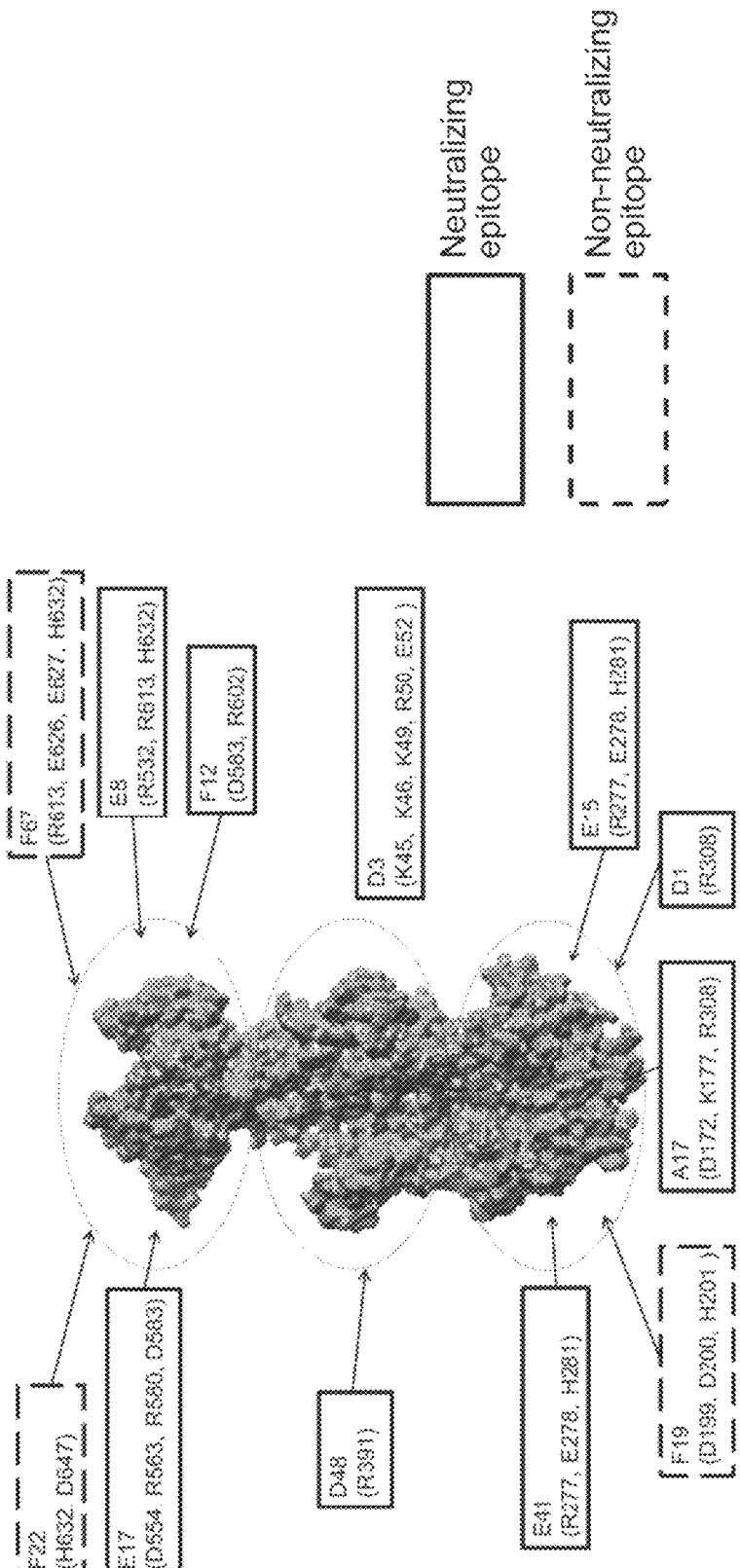
FIG. 3 is a MOE diagram of the results of identifying epitopes of gB antibodies by alanine scanning of Example 3.

Based on the binding activity of alanine substitutes and antibody fragments, the epitopes of each antibody were estimated. The results are shown in Table 2. There were 28 clones of antibodies to domain IV forming Crown portion of the gB trimer, which were most abundant. Subsequently, there were 8 clones of antibodies to domain I forming Bottom portion, and there was only one clone of antibody to domain II forming Middle portion. In the antibodies for which epitopes were able to be identified, many were at distant positions in the amino acid sequence. Although gB of HSV2 was modeled in MOE (FIG. 3) using gB of HSV1 as a template and their positions were confirmed, they were structurally proximate amino acids to each other (data not shown). For only D48 that recognizes domain II, R391 and D362 were identified, but since D48 reacts with gB37-457, R391 is likely to be the key of the epitope. The epitopes of 7 clones (E82, E88, F7, F65, F80, G10, G76) in 44 clones were not achieved to be identified. However, since there are clones, whose epitopes were able to be identified, in the same group by grouping of previous competitive ELISA or the like, it is likely that amino acid residues in the vicinity are their epitopes. For example, epitopes of E82 and E88 could not be identified, but it is known that the epitopes of E8 and E35 are R532, R613, H632. Since E82 and E88 compete with E8 and E35 in competitive ELISA, the epitopes of E82 and E88 are expected to be in the vicinity of R532, R613, H632. The antibodies whose epitopes were unable to be identified are considered that they likely have epitopes of amino acid residues other than charged amino acids from a viewpoint that this analysis is limited to charged amino acid residues.

TABLE 2

Identification of epitopes of anti-gB antibodies by alanine scanning

| Clone | Epitope | | | | Domain |
|---|---|---|---|---|---|
| A17 | D172 | K177 | R308 | | I |
| D1 | R308 | | | | I |
| D2 | R308 | | | | I |
| D3 | K45 | K46 | K49 | R50 | E52 | VI |
| D37 | K45 | K46 | K49 | R50 | E52 | VI |
| D48 | R391 | D362 | | | II |
| E7 | D583 | | | | IV |
| E8 | R613 | R537 | H632 | | IV |
| E15 | R277 | E278 | H281 | | I |
| E17 | D583 | D554 | R563 | R580 | IV |
| E31 | D583 | R563 | D554 | R277 | R379 | IV |
| E35 | R532 | H632 | R379 | | IV |
| E41 | R458 | R277 | E278 | H281 | I |
| E82 | ND | | | | IV |
| E88 | ND | | | | IV |
| F7 | ND | | | | IV |
| F11 | D583 | D554 | R563 | D258 | IV |
| F12 | D583 | R602 | | | IV |
| F13 | D200 | H201 | E259 | | I |
| F18 | D200 | D224 | K306 | | I |
| F19 | D199 | D200 | H201 | | I |
| F22 | H632 | | | | IV |
| F30 | D647 | H632 | | | IV |
| F33 | D583 | D554 | R563 | | IV |
| F52 | D583 | D554 | R563 | | IV |
| F65 | ND | | | | IV |
| F67 | E627 | E626 | R613 | H632 | IV |
| F68 | D583 | | | | IV |
| F69 | R580 | D583 | D554 | | IV |
| F75 | R567 | | | | IV |
| F78 | D199 | D200 | H201 | K401 | I |
| F80 | ND | | | | IV |
| F87 | H632 | | | | IV |
| G10 | ND | | | | IV |
| G25 | R567 | | | | IV |
| G39 | H632 | | | | IV |
| G64 | D554 | R563 | D583 | | IV |
| G65 | H632 | | | | IV |
| G76 | ND | | | | IV |
| H15 | D583 | D554 | R563 | | IV |
| H34 | D583 | D554 | R563 | | IV |
| H57 | D583 | R498 | | | IV |
| H61 | D583 | D554 | R563 | | IV |
| H65 | R580 | | | | IV |

ND: Not detected

Example 4 Analysis of the Presence of Neutralizing and Non-Neutralizing Epitopes in Crown and Bottom Portions of gB by Neutralization Test <Cells and Viruses>

Vero cells purchased from ATCC (CCL.81) were used for viral culture, measurement of infectivity titer, and measurement of neutralizing antibody titer. Human herpes virus 2 (HSV-2) MS strains [VR-540] were used for neutralization test and infection prevention ability analysis. For HSV-1, KOS strain (VR-1493) were purchased from ATCC and used. Vero cells were cultured in 10% FBS-containing MEM medium until full-sheeted, and the HSV-2 MS strain and HSV-1 KOS strain were inoculated at m.o.i=0.01-1. After culturing the cells in 2% FBS-containing MEM medium for 2-3 days, viruses in the cells were released into the medium by three freeze-thaws. After centrifugation, supernatants were collected and used as HSV-2 virus bank and HSV-1 virus bank.

<Viral Neutralization Test>

The neutralization activity of the acquired anti-gB clones was evaluated by viral neutralization test. The neutralization test was performed using two methods, a measurement of plaque number-reducing activity (plaque reduction activity) and a measurement of cell-to-cell infection spread-suppression activity. Two types of virus of interest, HSV-2 MS strain and HSV-1 KOS strain, were used. For the measurement of plaque reduction activity, a predetermined concentration of the subject antibody was prepared and mixed with about 100 PFU of HSV-2 MS strains or HSV-1 KOS strains, then reacted at 37° C. for 1 hour. The reaction solution was plated to Vero cells full-sheeted in a 48-well plate, and after adsorption at 30° C. for 1 hour, cultured in 1% methylcellulose-containing medium for 24 hours, then inactivation and immobilization were performed at −20° C. for 30 minutes with 50% methanol/50% ethanol (−20° C.) obtained by mixing methanol and ethanol at 1:1. The anti-HSV gB monoclonal antibody was then reacted at 37° C. for 1 hour, the resultant was immunostained with anti-mouse IgG-HRP (Dako P0447) and TMBH (MOS TMBH-1000), and images of each well were captured with an ELISpot analyzer to count plaque numbers with analytical software.

For the measurement of cell-to-cell infection spread-suppression activity, about 100 PFU of HSV-2 MS strain or HSV-1 KOS strain were inoculated into Vero cells full-sheeted in a 48-well plate, and adsorption was performed at 30° C. for 1 hour. Thereafter, a predetermined concentration of the subject antibody in 1% methylcellulose medium (antibody concentrations was 5 μg/mL, 25 μg/mL, and 125 μg/mL) was added. The HSV-2 MS strain was cultured for about 40 hours and the HSV-1 KOS strain was cultured for about 48 hours, then inactivation and immobilization were performed at −20° C. for 30 minutes with 50% methanol/50% ethanol (−20° C.). Anti-HSV gB monoclonal antibodies were then reacted at 37° C. for 1 hour, then the resulting cells were immunostained with anti-mouse IgG-HRP (Dako P0447) and TMBH, and images of each well were captured with an ELISpot analyzer to analyze average plaque size values with analytical software.

The results are shown in Table 3. The acquired 44 clones were categorized into two of neutralizing and non-neutralizing antibodies. Among the neutralizing antibodies, there were clones that neutralize both HSV-1 and HSV-2, type-specific clones that neutralize only one of them, clones with strong plaque number-reducing activity but no (weak) cell-to-cell infection spread-suppression activity, clones with strong both plaque number-reducing activity and cell-to-cell infection spread-suppression activity, and the like. It was also confirmed that this neutralization pattern is linked to the previous grouping results (Table 3, FIG. 2).

TABLE 3

Neutralization activities of anti-gB antibodies

| Clone | HSV-1 KOS strain | | HSV-2 MS strain | |
|---|---|---|---|---|
| | Plaque number reduction | Cell-to-cell spread suppression | Plaque number reduction | Cell-to-cell spread suppression |
| A17 | ++ | ++ | ++ | N.T. |
| D1 | ++ | ++ | − | − |
| D2 | ++ | ++ | − | − |
| D3 | − | − | ± | ± |
| D37 | − | − | ± | ± |
| D48 | ++ | ++ | ++ | ++ |
| E7 | ++ | ++ | ++ | ++ |
| E8 | − | − | − | − |
| E15 | ++ | ++ | ++ | ++ |
| E17 | ++ | − | ++ | ++ |
| E31 | ++ | − | ++ | ++ |
| E35 | ± | − | ± | − |
| E41 | ++ | ++ | ++ | ++ |
| E82 | − | − | − | − |
| E88 | ++ | N.T. | ++ | ++ |
| F7 | − | − | − | − |
| F11 | + | + | + | + |
| F12 | + | + | + | + |
| F13 | − | − | − | − |
| F18 | − | − | − | − |
| F19 | − | − | − | − |
| F22 | − | − | − | − |
| F30 | − | − | − | − |
| F33 | + | + | + | + |
| F52 | + | − | + | + |
| F65 | − | − | − | − |
| F67 | − | − | − | − |
| F68 | − | − | − | − |
| F69 | + | + | + | + |
| F76 | − | − | − | − |
| F78 | − | − | − | − |
| F80 | − | − | − | − |
| F87 | − | − | − | − |
| G10.3 | ± | − | ± | N.T. |
| G25 | − | − | − | N.T. |
| G39 | − | − | − | N.T. |
| G64 | ++ | ++ | ++ | N.T. |
| G65 | + | + | + | N.T. |
| G76 | + | + | + | N.T. |
| H15 | ++ | + | ++ | N.T. |
| H34 | ++ | + | ++ | N.T. |
| H57 | ++ | + | ++ | N.T. |
| H61-1 | ++ | + | ++ | N.T. |
| H65 | ++ | + | ++ | N.T. |

N.T.: Not tested

The plaque number-reducing activity was analyzed at 5 μg/mL, 25 μg/mL, and 125 μg/mL, and those with neutralizing ability at up to 5 μg/mL were determined to be "++", those with neutralizing ability at up to 25 μg/mL were determined to be "+", and those with neutralizing ability at up to 125 μg/mL were determined to be "±". The cell-to-cell infection spread-suppression was analyzed at 5 μg/mL, 10 μg/mL, and 20 μg/mL, and those with neutralizing ability at up to 5 μg/mL were determined to be "++", those with neutralizing ability at up to 10 μg/mL were determined to be "+", and those with neutralizing ability at up to 20 μg/mL were determined to be "±". All measurements were performed in duplicate.

From Table 2, antibodies to domains IV and I on the gB2 antigen accounted for a large percentage to the total antibody. The antibodies to domains IV and I were partially with neutralizing activity, but mostly non-neutralizing antibodies that did not exhibit neutralizing activity (Table 3). In contrast, antibodies to domain II accounted for a small percentage to the total antibody, but they were neutralizing antibodies. In the MOE diagram (FIG. 3) which is the identification result of epitopes of each gB antibody, positions of these epitopes are illustrated. From these results, it was revealed that neutralizing epitopes and non-neutralizing epitopes are present in domains IV and I, and neutralizing epitopes are present in domain II, and that many "conspicuous" antigen epitopes are present in domains IV and I.

Example 5 Design and Evaluation of Vaccine Antigens

<Design Strategy of Modified gB Antigen>

Figure 4:
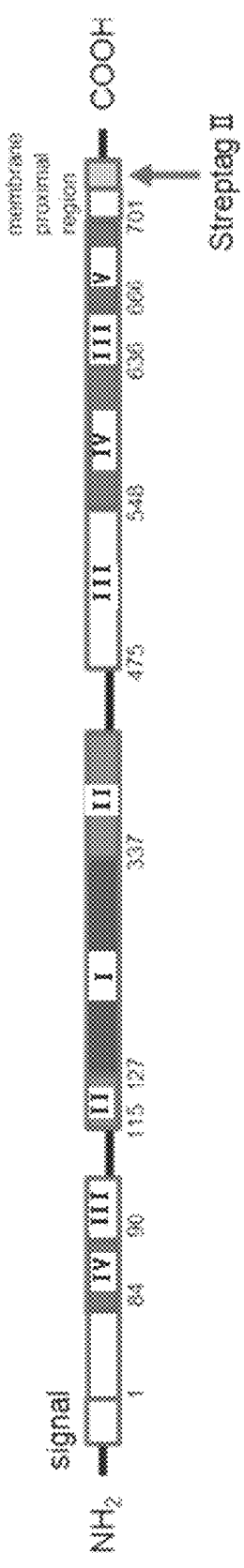
FIG. 4 is a diagram illustrating a schematic for a design strategy of a modified gB protein of Example 5.
Figure 4:
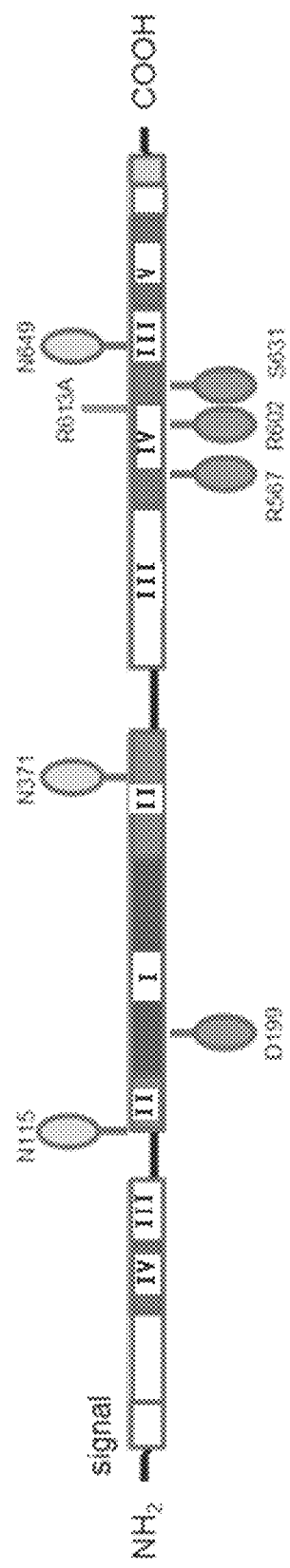

Comprehensive acquisition of anti-HSV2-gB antibodies and their epitope mapping and functional classification were performed. As the result, it was found that neutralizing epitopes and non-neutralizing epitopes are present in domain IV and domain I, and neutralizing epitopes are present in domain II in the gB2 antigen. From the viewpoint of preventive activity expression, modified gB antigens were designed by setting the neutralizing epitopes as beneficial epitopes, and the non-neutralizing epitopes as unbeneficial or deleterious epitopes, and de-epitoping the non-neutralizing epitopes present in gB domains I and IV. The base wild-type gB was the ectodomain gB1-705, and Streptag II was added to the C-terminal side for StrepTactin purification (FIG. 4(A)).

Figure 5:
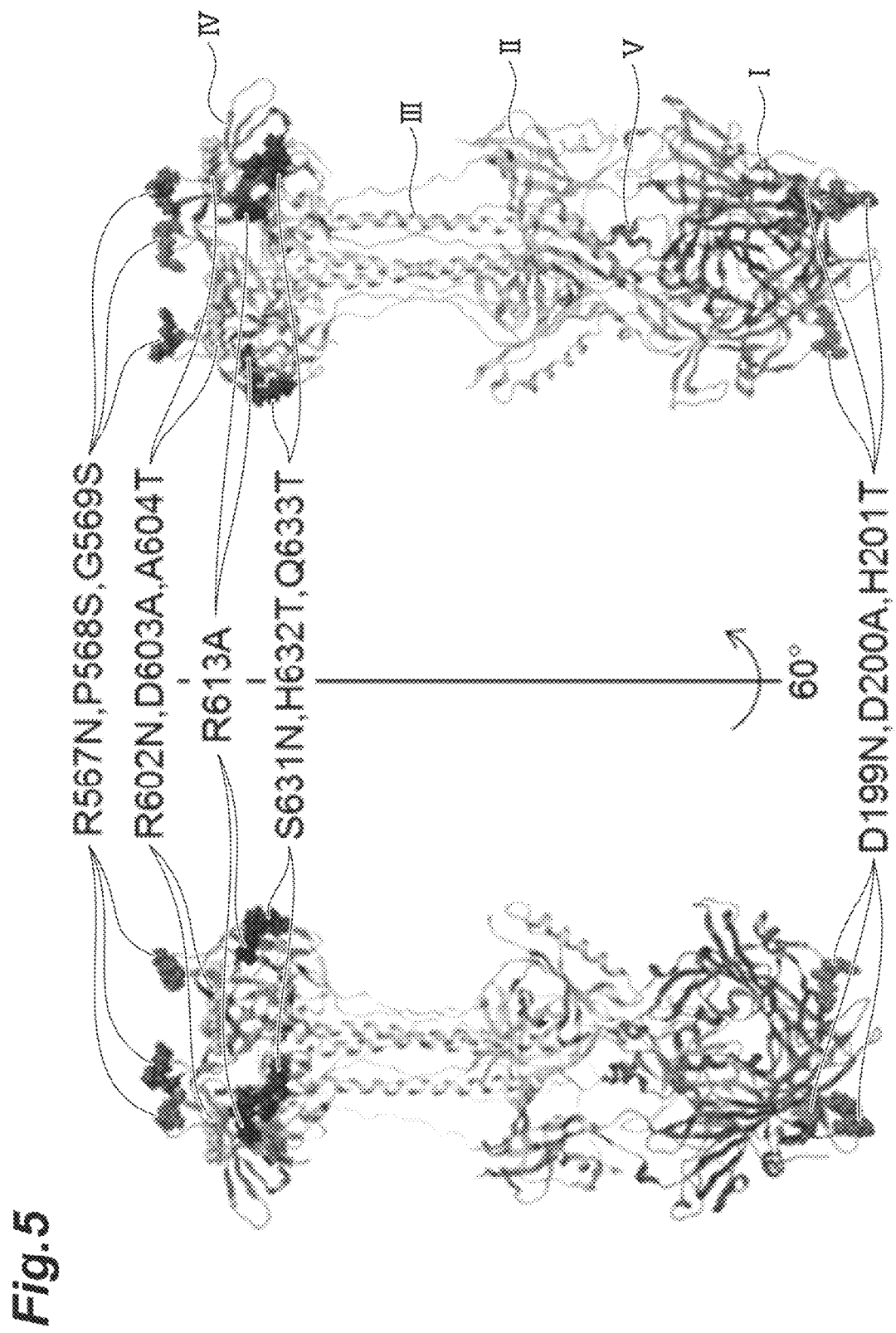
FIG. 5 is a diagram illustrating a simplified schematic of a crystal structure for a design strategy of a modified gB protein of Example 5.

First, the modification of gB by N-type glycosylation was considered. The N-type glycochain, unlike 0-type glycochain, is added to a consensus sequence, NXT or NXS (X is any amino acid other than proline). Antibodies are generally difficult to be generated against glycopeptides, and due to the bulkiness of the glycochain, antibodies are also difficult to be generated against peripheries of the glycopeptides (Non Patent Literature 16). Domain IV of HSV2-gB is thought to be an important region for binding to the receptor, but is furthest away from the surface of the viral membrane and is exposed to the surface so that it is susceptible to antibody binding. Indeed, as shown in the result described above, it has been suggested that many antibodies that recognize domain IV are contained in human serum. Thus, it was decided to introduce an N-type glycochain at three locations of the non-neutralizing epitopes in domain IV (FIGS. 4(B) and 5). Meanwhile, domain I is located at the root of gB and is an important region for fusion with the host cell, but when only the ectodomain is expressed, the region that has been originally in contact with the viral membrane surface is exposed to the surface. In addition, the vaccine antigen design using only ectodomain of gB is assumed in the manufacture of vaccines. There is a possibility that a region in contact with the viral membrane may be newly exposed, thus it was decided to introduce an N-type glycochain at one location of the non-neutralizing epitope region (FIGS. 4(B) and 5). The glycochains originally attached to the wild-type gB appear to be positioned at N115, N371, N649 with reference to HSV-1 gB (PDB No. 3 NWF) (FIG. 4(B)). Thus, D199, R567, R602, S631 were newly selected as positions for introducing a glycochain.

Next, the modification of gB by alanine substitution was considered. Charged amino acid residues are often included as epitopes of antibodies. Thus, a method for de-epitoping by substituting a charged amino acid residue with a non-characteristic amino acid residue is sometimes taken. This method, unlike the introduction of an N-type glycochain, has an advantage that it can achieve de-epitoping by pinpoint. Not only non-neutralizing epitopes but also neutralizing epitopes are present in domain IV, thus it was decided to perform alanine substitution at one location (R613A) to be performed (FIGS. 4(B) and 5).

<Preparation of Modified gB1-705>

The cDNA (SEQ ID NO: 4) of gB ectodomain (1-705aa) derived from wild-type HSV-2 333 strain was cloned into pCAGGS1-dhfr-neo. The gB was designed so that Streptag II is added to the C-terminal. Using this sequence as a template, variants in which the following mutations were introduced were designed:

Modified product bcev1-3: D199N, D200A, H201T
Modified product bceg13: R567N, P568S, G569S
Modified product bcev11: D199N, D200A, H201T, R613A
Modified product bcev12: D199N, D200A, H201T, R567N, P568S, G569S, R613A
Modified product bcev13: D199N, D200A, H201T, R567N, P568S, G569S, R613A, S631N, H632A, Q633T
Modified product bcev19: D199N, D200A, H201T, R567N, P568S, G569S, R613A, S631N, H632T, Q633T
Modified product bcev19': R567N, P568S, G569S, R613A, S631N, H632T, Q633T
Modified product bcev50: D199N, D200A, H201T, R567N, P568S, G569S, R613A, R602N, D603A, A604T, S631N, H632T, Q633T
Modified product bcev50': R567N, P568S, G569S, R613A, R602N, D603A, A604T, S631N, H632T, Q633T For expression, a FreeStyle 293 or Expi 293 expression system was used. Expression plasmids were transfected into cells and culture supernatants were collected at 4-6 days. The culture supernatant containing gB was concentrated with a UF membrane to suppress the effects of biotin contained in the medium. The concentrated culture supernatant was purified with a StrepTactin column to acquire purified gB.

For properties of the acquired purified gB1-705, the multimeric state thereof was determined by SDS-PAGE and gel filtration chromatography. In the gel filtration chromatography, Superdex 200 Increase 5/150 GL (GE Healthcare) was used as the column, and each modified gB purified product was applied at a concentration of 100 µg/mL. D-PBS was used as the electrophoresis buffer at a flow rate of 0.4 mL/min to detect A280.

Table 4 shows the modification sites and characteristics of the six modified gB s.

introducing a glycochain into domain I was added, and the expression level thereof is enhanced approximately 2-fold compared to that of wild-type gB1-705. It is believed that this region is originally stabilized in a state contact with the surface of the viral membrane. It is presumed that the wild-type gB1-705 is destabilized due to secretion expression which leads to the exposure of this region that is not otherwise solvent contacted, then by the addition of a glycochain to the region, bcev1-3 is stabilized to increase the expression level.

The bceg13 is a gB to which modifications of R567N, P568S, G569S were added in domain IV. In contrast to bcev1-3, the expression level thereof is 0.3-fold compared to that of wild-type gB1-705. Since the trimeric structure similar to that of the wild-type is maintained, it is suggested that mutation is not a critical mutation to maintain the structure, but the single-chain structural changes and folding thereof is slower than those of the wild-type.

The bcev11 is a variant in which, in addition to the D199N, D200A, H201T mutations in bcev1-3, R613A positioned in domain IV were introduced. The expression level of bcev11 was equivalent to that of wild-type gB1-705.

Given that the bcev1-3 mutation enhanced the expression level, it is suggested that the R613A mutation is a contrary mutation that makes expression level reduced or equal to that of the wild-type.

The properties of bcev11 were also equivalent to those of the wild-type and a trimer thereof was formed.

The bcev12 is a gB in which further modifications of R567N, P568S, G569S were added to bcev11. Based on the result of bceg13, the addition of R567N, P568S, G569S mutations should have reduced the expression level, but expression level thereof unexpectedly doubled compared to that of the wild-type. This expression level is equivalent to that of bcev1-3 in which only modifications of D199N, D200A, H201T were added. It is suggested that R613A mutation contributes to reduction of expression level, but the addition of R567N, P568S, G569S makes the structure and folding rate of domain IV closer to bcev1-3.

The bcev19 is a gB variant in which mutations of S631N, H632T, Q633T were introduced into bcev12. The expression level of bcev19 was 0.6-fold compared to that of wild-type, and not only trimer but also trace amounts of multimer were

TABLE 4

| Clone | Mutation site | Expression level (µg/mL) | Multimeric state | Artificial glycochain introduction |
|---|---|---|---|---|
| gB1-705 (Wild-type) | — | 2.25 | Trimer | 0 |
| bcev1-3 | D199N, D200A, H201T | 4.18 | Trimer | 1 |
| bceg13 | R567N, P568S, G569S | 0.64 | Trimer | 1 |
| bcev11 | D199N, D200A, H201T, R613A | 2.04 | Trimer | 1 |
| bcev12 | D199N, D200A, H201T, R567N, P568S, G569S, R613A | 4.01 | Trimer | 2 |
| bcev19 | D199N, D200A, H201T, R567N, P568S, G569S, R613A, S631N, H632T, Q633T | 1.38 | Multimer Trimer | 3 |
| bcev50 | D199N, D200A, H201T, R567N, P568S, G569S, R613A, R602N, D603A, A604T, S631N, H632T, Q633T | 0.35 | Multimer Trimer | 4 |

N.T.: Not tested

The bcev1-3 to which D199N, D200A, H201T modifications were added is a gB modified to which a mutation of contained therein. Other mutations to S631, H632, Q633 or glycosylation to a vicinity location other than 631-633aa were also examined, but no significant improvement effect on the properties was observed (data not shown).

The bcev50 is a gB variant in which mutations of R602N, D603A, A604T were introduced into domain IV of bcev19. The expression level thereof was further reduced compared to that of bcev19 and 0.3-fold compared to that of wild-type.

Fc/HRP (Rockland Immunochemicals, Inc.) was added to the wells of the plate and incubated at 37° C. After 1 hour, the plate was washed with PBST and colored by adding 100 µL of TMB to the wells of the plate. After 30 minutes, the reaction was stopped with 1N sulfuric acid, and absorbance (O.D. 450 nm/650 nm) was measured with a microplate reader.

The results are shown in Table 5.

TABLE 5

Reactivities of the modified gB and acquired antibodies

|  | Ab Clone | gB1-705 | bcev1-3 | bceg13 | bcev11 | bcev12 | bcev19 | bcev50 |
|---|---|---|---|---|---|---|---|---|
| Non-neutralizing antibodies | F22 | + | + | + | + | + | − | − |
|  | F30 | + | + | + | N.T. | ± | − | − |
|  | F7 | + | + | + | N.T. | + | + | − |
|  | F65 | + | + | + | N.T. | + | ± | − |
|  | F67 | + | + | + | ± | − | − | − |
|  | F68 | + | + | + | N.T. | + | + | − |
|  | F76 | + | + | − | N.T. | − | − | − |
|  | F80 | + | + | + | N.T. | ± | ± | − |
|  | F87 | + | + | + | N.T. | − | − | − |
|  | G39 | + | + | + | N.T. | ± | − | − |
|  | G76 | + | + | + | N.T. | − | ± | − |
|  | G65 | + | + | + | N.T. | − | − | − |
|  | E8 | + | + | + | − | − | − | − |
|  | E35 | + | + | + | N.T. | + | − | − |
|  | E82 | + | + | + | N.T. | − | − | − |
|  | E88 | + | + | + | N.T. | − | − | − |
|  | G25 | + | + | − | + | − | − | − |
|  | F13 | + | − | + | − | − | − | − |
|  | F18 | + | + | + | N.T. | ± | + | − |
|  | F19 | + | − | + | N.T. | − | ± | − |
|  | F78 | + | − | ± | N.T. | − | ± | − |
| Neutralizing antibodies | E7 | + | + | + | N.T. | + | + | ± |
|  | E17 | + | + | + | N.T. | + | + | + |
|  | E31 | + | + | + | + | + | + | − |
|  | F11 | + | + | + | N.T. | + | + | − |
|  | F12 | + | + | + | + | + | + | − |
|  | F33 | + | + | + | N.T. | + | + | ± |
|  | F52 | + | + | + | N.T. | + | + | ± |
|  | F69 | + | + | + | + | + | + | − |
|  | G64 | + | + | + | N.T. | + | + | + |
|  | H15 | + | + | + | N.T. | + | + | − |
|  | H34 | + | + | + | N.T. | + | + | ± |
|  | H57 | + | + | + | N.T. | + | + | ± |
|  | H61 | + | + | + | N.T. | + | + | − |
|  | H65 | + | + | + | N.T. | + | + | − |
|  | G10 | + | + | + | N.T. | − | − | − |
|  | D3 | + | + | + | ± | + | + | + |
|  | D37 | + | + | + | N.T. | + | + | + |
|  | D48 | + | + | + | + | + | + | + |
|  | E15 | + | + | + | + | + | + | + |
|  | D1 | + | + | + | + | + | + | ± |
|  | D2 | + | ± | + | N.T. | ± | + | ± |
|  | A17 | + | + | + | + | + | + | + |
|  | E41 | + | + | + | + | + | + | − |

N.T.: Not tested

For properties, trimers were contained as in bcev19, but multimers were also contained.

<Binding Activity Test of Modified gB1-705>

To confirm the aim of low or no reactivity with non-neutralizing antibodies, the reactivity of the produced variants bcev1-3, bceg13, bcev12, bcev19 and bcev50 with 44 clones of the anti-gB2 monoclonal antibody was evaluated by ELISA. As a control, wild-type gB1-705 was used. The gB1-705 was diluted with PBS to 1 µg/mL, then 50 µL of the dilution was placed in Maxisorp Plate, and incubated at 4° C. overnight to make gB1-705 immobilized. After the immobilization, the plate was washed with PBS, and 100 µL of the acquired antibody was added to wells of the plate and incubated at 37° C. After 1 hour, the plate was washed with PBST, and 100 µL of the detection antibody anti-human IgG The bcev1-3 was no longer reactive with F13, F19, F78 whose epitope is D200, H201 after mutations of D199N, D200A, H201T were introduced. The bceg13 was no longer reactive with F76, G25 whose epitope is R567 after mutations of R567N, P568S, G569S were introduced.

The bcev12 into which the modifications of bcev1-3 and bceg13 and R613A were introduced was almost no longer reactive with antibodies whose epitopes are each mutation site.

The bcev19 in which mutations of S631N, H632A, Q633T were introduced into bcev12 maintained reactivity with 22 types of neutralizing antibodies, while became less reactive with non-neutralizing antibodies.

Among the 21 types of non-neutralizing antibodies, a total 8 type, F7, F65, F68, F80 and G76 which recognize domain IV and F18, F19 and F78 which recognize domain I, maintained reactivity.

The bcev50 in which mutations of R602N, D603A, A604T were introduced into bcev19 was no longer reactive with all 21 types of non-neutralizing antibodies. Meanwhile, for the 23 types of neutralizing antibodies, it maintained reactivity with 14 types, but became less reactive with 9 types.

These mean a possibility that immunizing the bcev50 makes not only non-neutralizing antibodies difficult to induce, but also neutralizing antibodies slightly difficult to induce. The difference between bcev19 and bcev50 is whether or not there are R602N, D603A, A604T mutations in domain IV. Nevertheless, differences have arisen in reactivity with antibodies to domain I. It is suggested that modification of domain IV keeps the trimer but may change the structure of domain I. In summary, bcev19 and bcev50 are less likely to generate non-neutralizing antibodies compared to wild-type antigen, gB1-705, and can be expected to be novel vaccine antigens that can induce an ideal immune response.

<Mouse Immunogenicity Test of Bcev19 and Bcev50>

Mouse immunogenicity tests of the produced modified gB antigens bcev19 and bcev50 were performed separately. In both experiments, mice were subcutaneously immunized with antigen dose of 0.3 µg/mouse and 1 µg/mouse at 2-week intervals for 3 times. The experiment was performed setting the number of mouse cases in each group as n=4.

An immunogenicity test of the modified gB antigen was performed using the wild-type gD antigen gB1-705 (gB WT) as a positive control and saline as a negative control. The predetermined amount of antigen was dissolved in saline for injection (saline) to immunize BALB/c mouse (5 weeks old, female) subcutaneously in back at a volume of 200 µL/mouse with MPLA (10 µg/mouse) and CpG (1 µg/mouse) at 2-week intervals for a total of 3 times. Two weeks after the final immunization (third dose), blood was collected for each individual and serum was prepared. The prepared serum was serially diluted, and the binding antibody titer to wild-type gB antigen (anti-gB ELISA) and neutralizing antibody titer against HSV-2 (50% plaque number-reducing activity) were evaluated.

Figure 6:
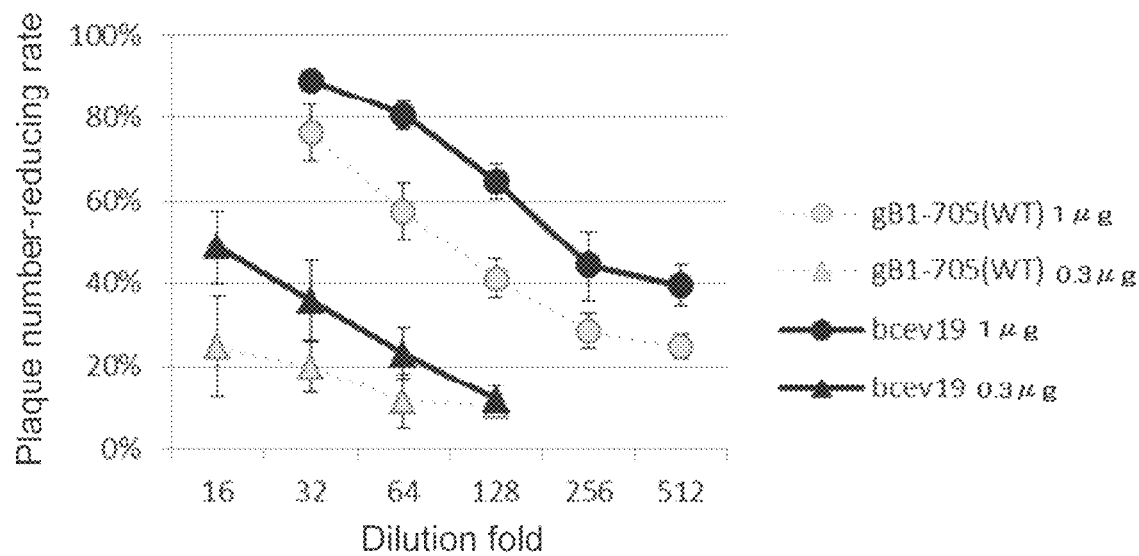
FIG. 6 is a diagram showing the result of the mouse immunogenicity test of bcev19 in Example 5.
Figure 6:
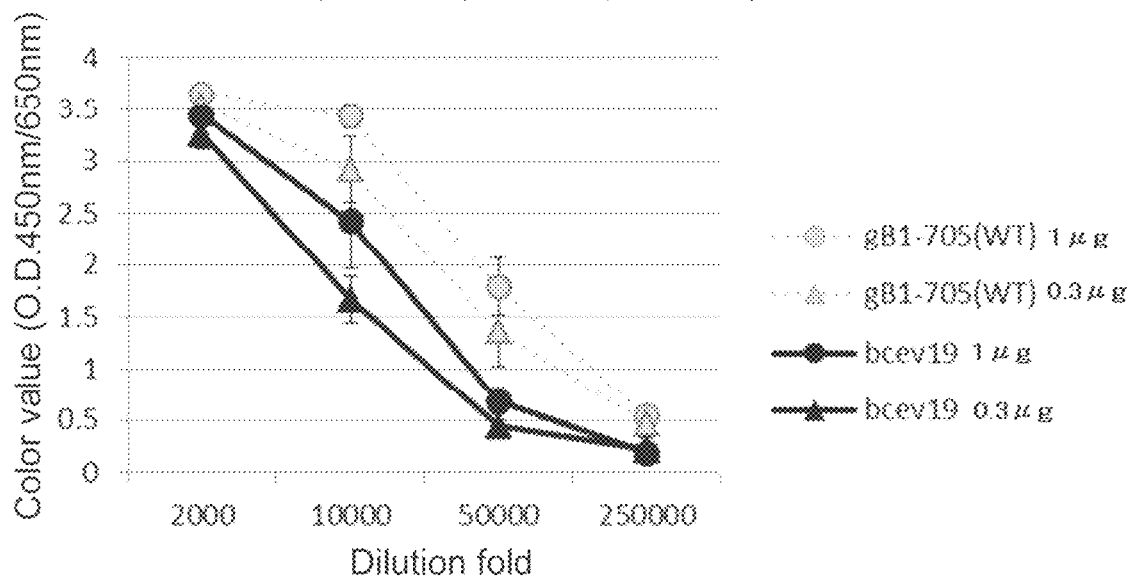
Figure 7:
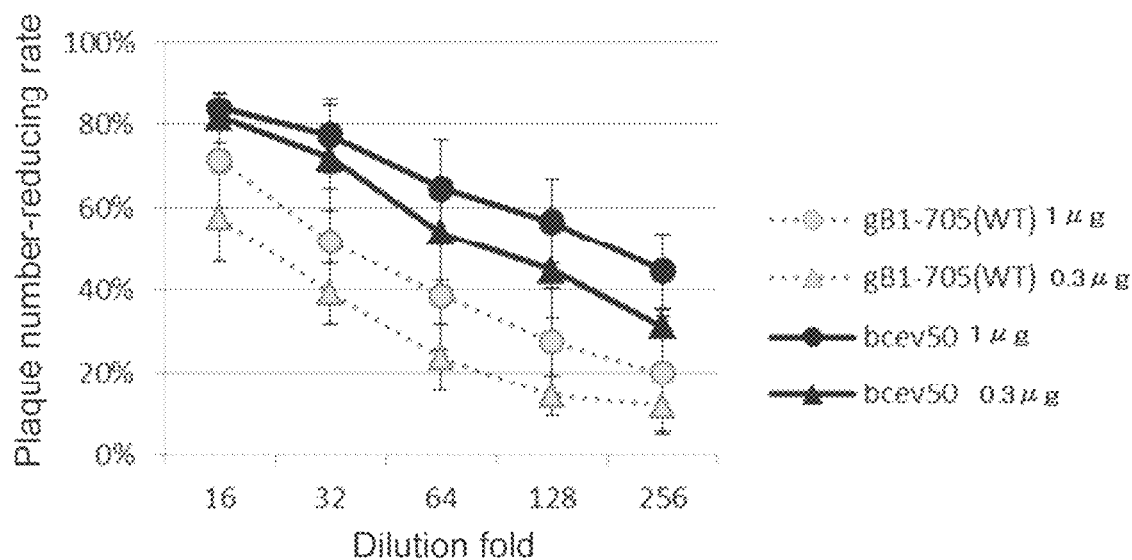
FIG. 7 is a diagram showing the result of the mouse immunogenicity test of bcev50 in Example 5.
Figure 7:
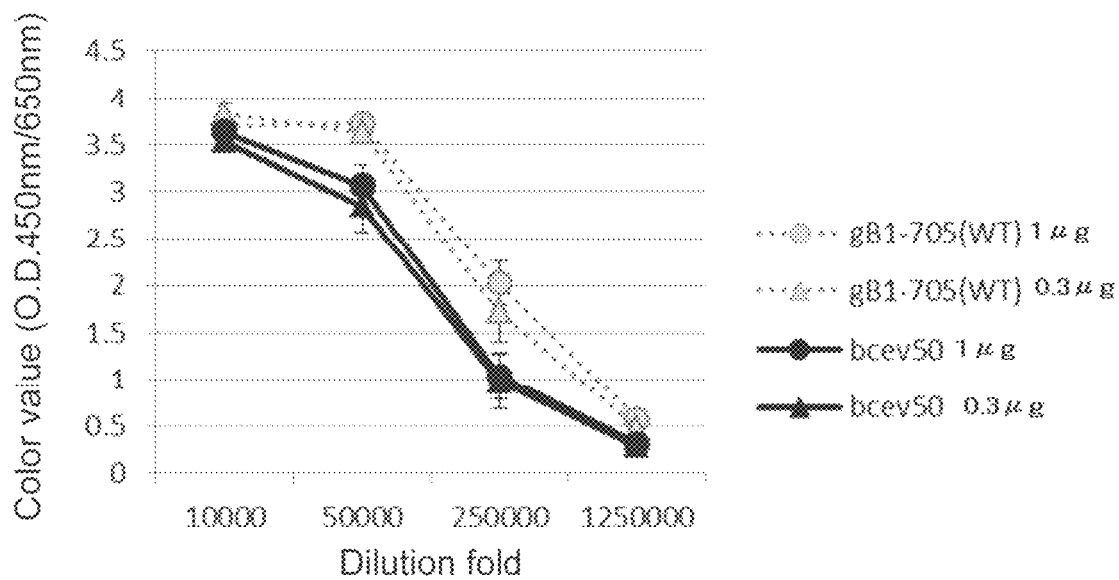

The result of bcev19 is shown in FIG. 6 and the result of bcev50 is shown in FIG. 7. In the graph, mean values of n=4 are plotted with ±SE error bars. Using serum collected 2 weeks after the final immunization, the binding antibody-inducing activity against wild-type gB antigen (anti-gB ELISA) and neutralizing antibody-inducing activity against HSV-2 (plaque number-reducing rate) were evaluated. As the result, both bcev19 and bcev50 were confirmed to induce higher neutralizing antibody activity with less binding antibody activity than wild-type gB antigen (gB1-705) at any dose.

The results are believed to be a result of being able to more efficiently and effectively induce an immune response to the remaining neutralizing epitopes (beneficial epitopes) by de-epitoping non-neutralizing epitopes (deleterious and unbeneficial epitopes) in the wild-type gB antigen by introduction of N-type glycosylation and alanine substitution. In other words, a biased immune response (immune deviation) to a wild-type gB antigen can have been ideally corrected (immune correction) by the present inventors' immune refocusing strategies.

<Mouse Infection-Prevention Test of Bcev19 and Bcev50>

An infection prevention ability in the preventive administration of modified gB antigens bcev19 and bcev50 was evaluated separately using a mouse genital herpes infection model. In both experiments, wild-type gB1-705 (gB WT) was used as a positive control. Mice were immunized subcutaneously with 0.03 µg/mouse, 0.1 µg/mouse, 0.3 µg/mouse, and 1 µg/mouse for all antigens at 2-week intervals for 3 times. Depo-Provera was inoculated subcutaneously at 2 mg/mouse 6 days prior to viral inoculation to improve multiplicity of infection upon viral inoculation 2 weeks after the final immunization (third dose). Mouse was inoculated transvaginally with $5 \times 10^5$ PFU/20 µL/mouse HSV-2 MS strain under anesthesia and observed for 21 days. The infection prevention ability was evaluated using survival time (survival rate) and symptom score as indexes. Symptom scores were classified by the extent of vaginal lesion symptoms and systemic symptoms, and scores were set for 3 and 2 stages, respectively. The total of the following vaginal lesion and systemic symptom scores were taken as the symptom scores: score for vaginal lesions (0: no change, 1: partial erythema/swelling, 2: extensive swelling/edema, 3: ulceration/bleeding); score for systemic symptoms (0: no change, 1: piloerection, 2: hind limb paralysis). Furthermore, death or sacrifice was scored 6. The experiment was performed setting the number of mouse cases in each group as n=10 and their mean values were plotted in the graph.

Figure 8:
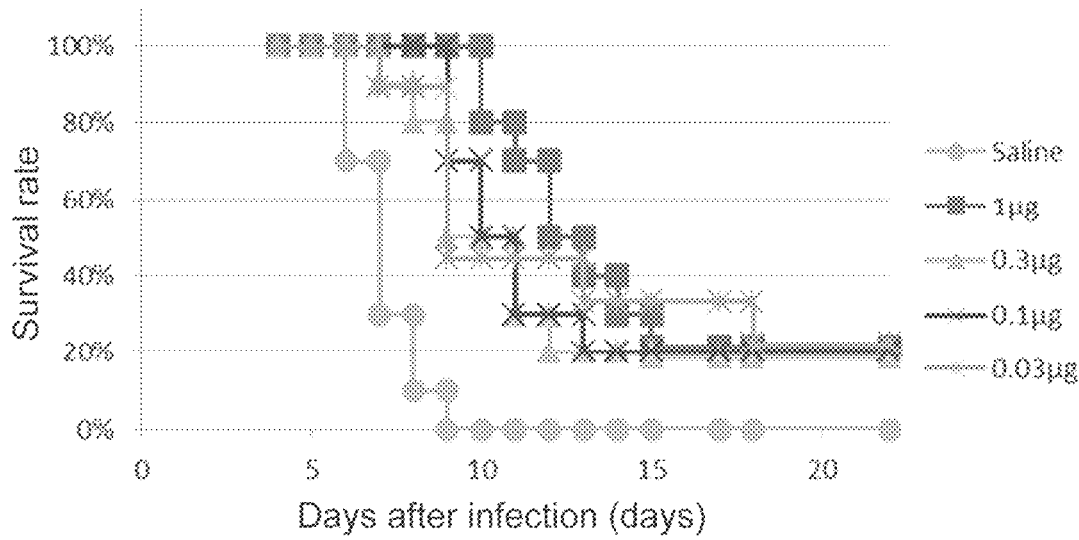
FIG. 8 is a diagram showing the result of survival rate of the mouse infection-prevention test of bcev19 in Example 5.
Figure 8:
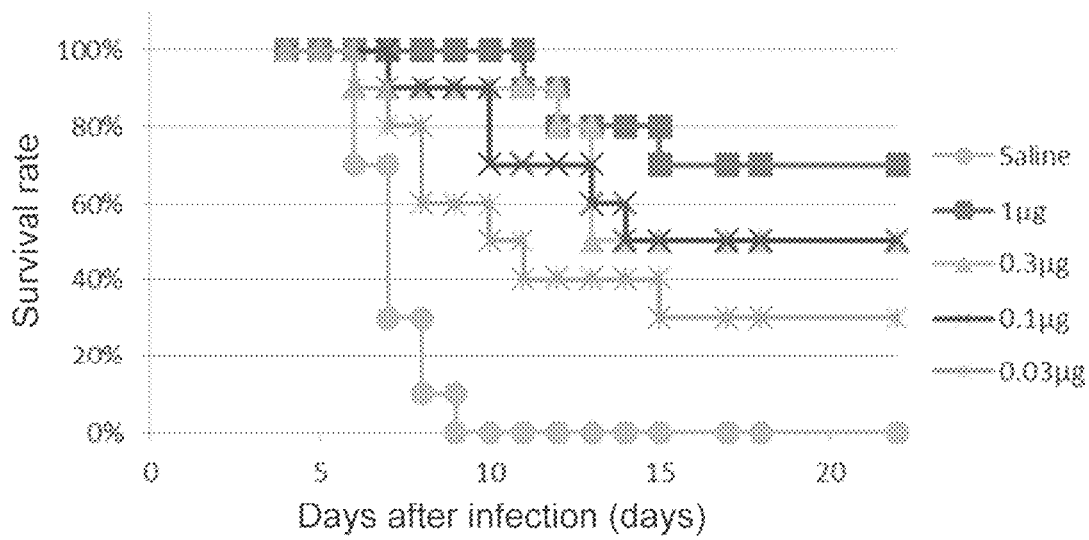
Figure 9:
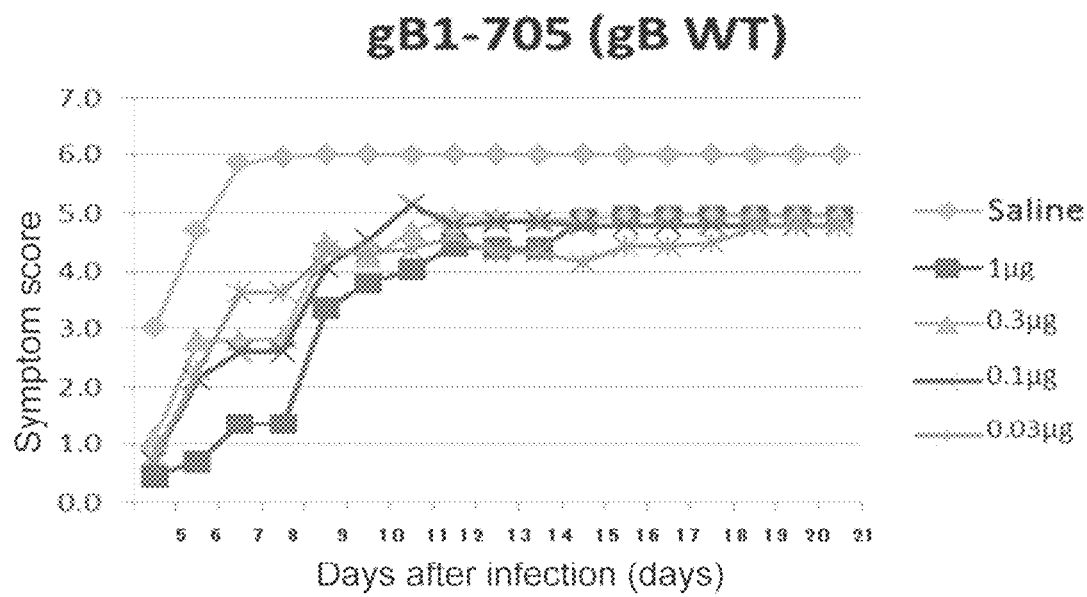
FIG. 9 is a diagram showing the result of symptom score of the mouse infection-prevention test of bcev19 in Example 5.
Figure 9:
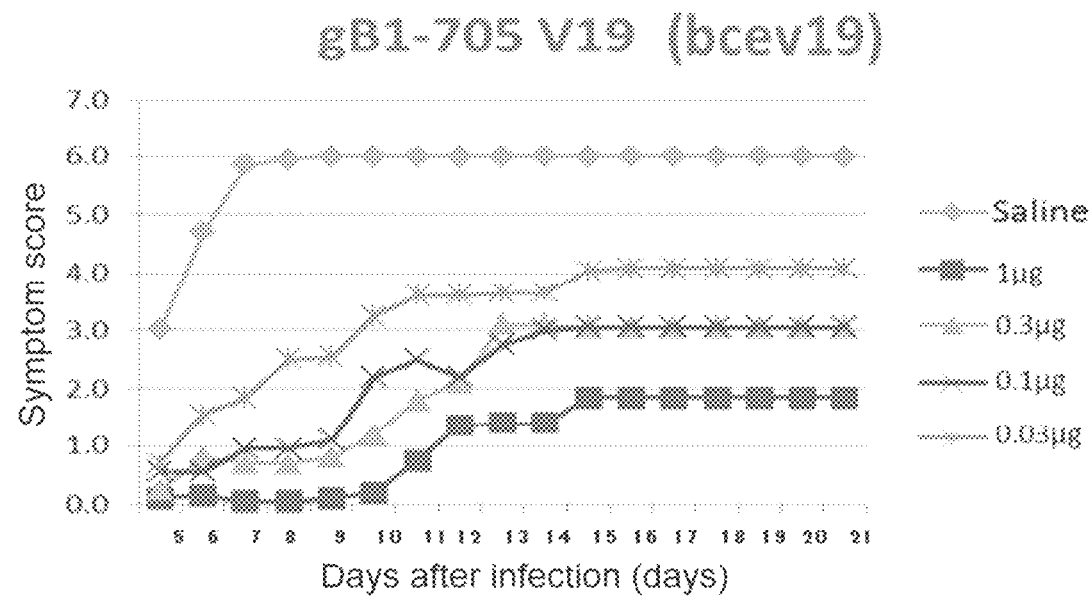

The results of bcev19 are shown in Table 6 (survival time), FIG. 8 (survival rate), and FIG. 9 (symptom score). In both of gB WT and bcev19, a significant survival time prolongation effect relative to the negative control group (saline administration group) was shown at all set dosages (0.03 to 1 µg/mouse). However, in the gB WT administration group, median survival time (MST) showed no clear dose dependency and the MST ratio to the saline administration group remained below 2 at any dosage. In contrast, in the bcev19 administration group, MST showed approximately dose dependency, and MST ratios were >2.8 at three doses of 0.1 µg/mouse or more, indicating clear improvement in survival rate (Table 6, FIG. 8). For the symptom score, in the gB WT administration group, there was no clear dose dependency and severe symptoms were accompanied even in the highest dose of 1 µg/mouse. However, in the bcev19 administration group, dose-dependent and significant improvement effects were observed (FIG. 9).

TABLE 6

| Antigen | Dosage (µg) | Survival days (days) | MST (days) | MST ratio (vs saline) | Significant difference test (vs saline) |
|---|---|---|---|---|---|
| gB1-705 (WT) | 1 | 9.9, 10, 11, 11, 12, 13, 14, >21, >21 | 11.5 | 1.9 | *** |
|  | 0.3 | 6, 7, 8, 8, 8, 10, 10, 11, >21, >21 | 9 | 1.5 | ** |
|  | 0.1 | 8, 8, 8, 9, 9, 10, 10, 12, >21, >21 | 9.5 | 1.6 | *** |
|  | 0.03 | 6, 8, 8, 8, 8, 11, 17, >21, >21 | 8 | 1.3 | ** |

TABLE 6-continued

| Antigen | Dosage (µg) | Survival days (days) | MST (days) | MST ratio (vs saline) | Significant difference test (vs saline) |
|---|---|---|---|---|---|
| bcev19 | 1 | 10, 11, 14, >21, >21, >21, >21, >21, >21, >21 | >21 | >3.5 | *** |
| | 0.3 | 5, 11, 12, 12, 12, >21, >21, >21, >21, >21 | >16.5 | >2.8 | *** |
| | 0.1 | 6, 9, 9, 12, 13, >21, >21, >21, >21, >21 | >17 | >2.8 | *** |
| | 0.03 | 5, 6, 7, 7, 9, 10, 14, >21, >21, >21 | 9.5 | 1.6 | * |
| saline | | 5, 5, 5, 6, 6, 6, 7, 7, 8 | 6 | | |

MST: Mean survival time
*: p < 0.0001/: 0.0001 < p < 0.001/*: 0.001 < p < 0.01 (Kaplan-Meier method)

Figure 10:
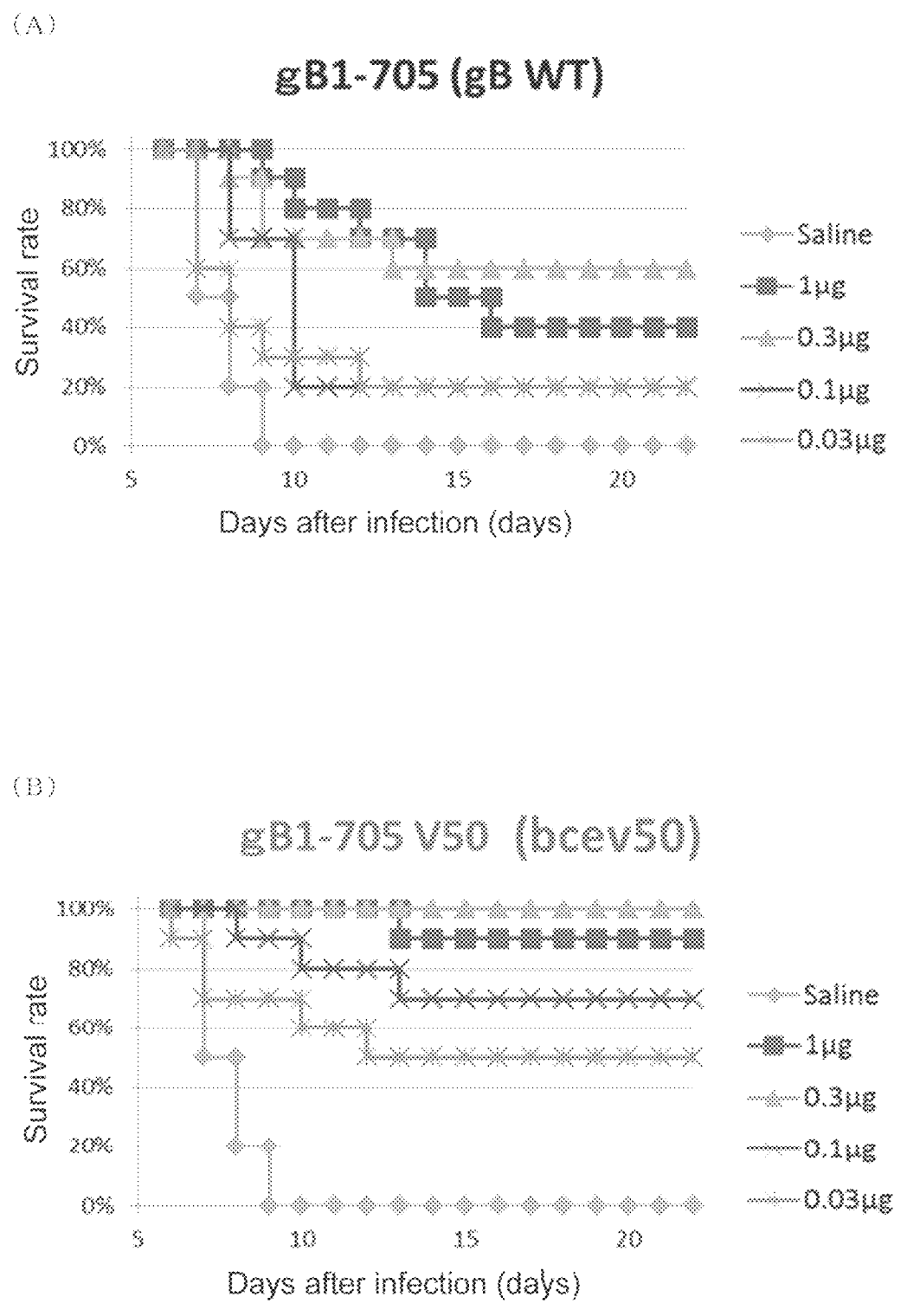

The results of bcev50 are shown in Table 7 (survival time), FIG. 10 (survival rate), and FIG. 11 (symptom score). Similar to bcev19, bcev50 also showed a clear superiority to gB WT in any index of survival time, survival rate, and symptom score.

TABLE 7

| Antigen | Dosage (µg) | Survival time (days) | MST (days) | MST ratio (vs saline) | Significant difference test (vs saline) |
|---|---|---|---|---|---|
| gB1-705 (WT) | 1 | 8, 9, 11, 13, 15, >23, >23, >23, >23 | 15 | 2.3 | *** |
| | 0.3 | 7, 8, 8, 12, >23, >23, >23, >23, >23, >23 | >23 | >3.5 | ** |
| | 0.1 | 7, 7, 7, 9, 9, 9, 9, 9, >23, >23 | 9 | 1.4 | ** |
| | 0.03 | 6, 6, 6, 6, 7, 7, 8, 11, >23, >23 | 7 | 1.1 | N.S. |
| bcev50 | 1 | 12, >23, >23, >23, >23, >23, >23, >23, >23 | >23 | >3.5 | *** |
| | 0.3 | >23, >23, >23, >23, >23, >23, >23, >23, >23, >23 | >23 | >3.5 | *** |
| | 0.1 | 7, 9, 12, >23, >23, >23, >23, >23, >23, >23 | >23 | >3.5 | *** |
| | 0.03 | 5, 6, 6, 9, 11, >23, >23, >23, >23, >23 | >17 | >2.6 | * |
| saline | | 6, 6, 6, 6, 6, 7, 7, 7, 8, 8 | 6.5 | | |

MST: Mean survival time
*: p < 0.0001/: 0.0001 < p < 0.001/*: 0.001 < p < 0.01 (Kaplan-Meier method)

<Analysis of Immune Refocusing>

For immune sera of the modified gB antigens bcev19 and bcev50, which were found to be superior to wild-type gB (gB1-705) in the mouse immunogenicity test and the mouse infection-prevention test, whether immune refocusing was induced or not was analyzed by gB1-457 and gB111-457 immobilized ELISAs, respectively.

Figure 12:
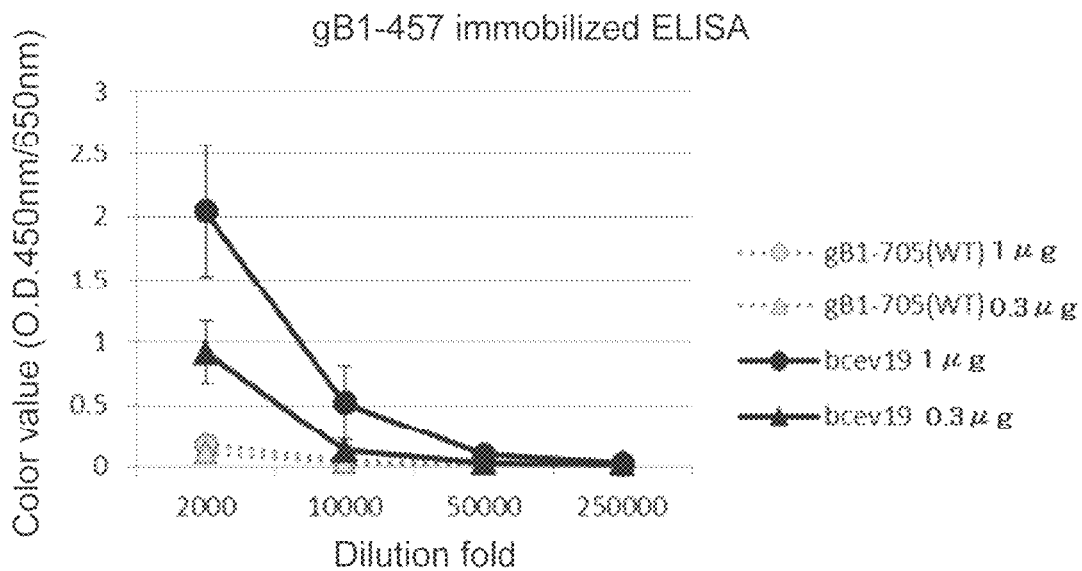
FIG. 12 is a diagram showing the analysis result of immune refocusing of bcev19 in Example 5.
Figure 12:
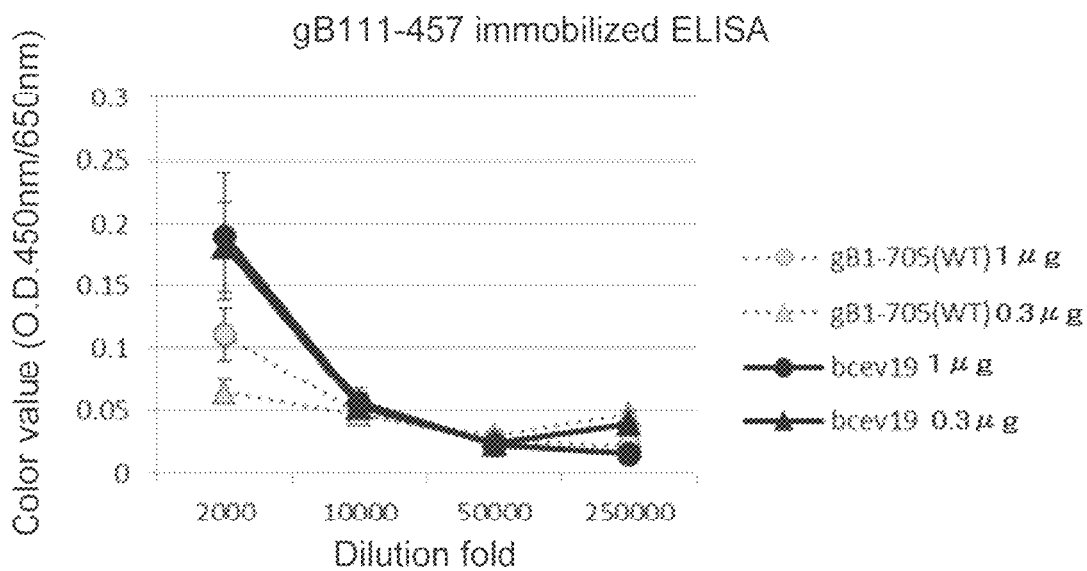
Figure 13:
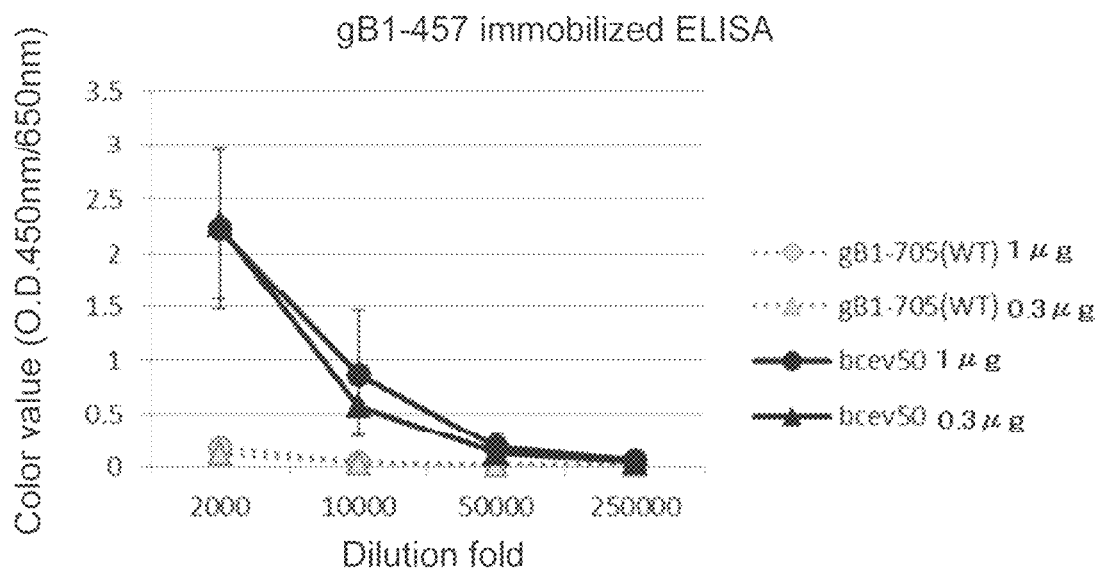
FIG. 13 is a diagram showing the analysis result of immune refocusing of bcev50 in Example 5.
Figure 13:
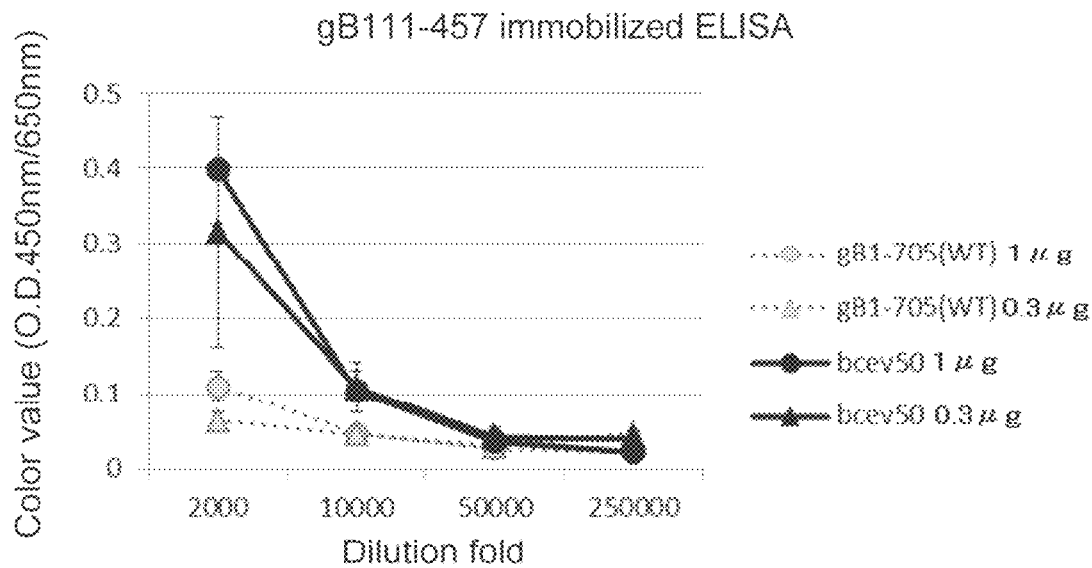

The analysis result of bcev19 is shown in FIG. 12 and the analysis result of bcev50 is shown in FIG. 13. Both bcev19 immune serum and bcev50 immune serum were confirmed to have increased binding antibody activity against gB1-457 and gB111-457 compared to wild-type gB immune serum. The above results are believed to be a result of being able to more efficiently and effectively induce an immune response to the neutralizing epitopes (beneficial epitopes) remaining a lot in domains I and II by de-epitoping the non-neutralizing epitopes present mainly in domain IV, which is thought to be a decoy region in wild-type gB antigen, by introduction of N-type glycosylation and alanine substitution. In other words, it is believed that a biased immune response (immune deviation) to the decoy region in the wild-type gB antigen can have been ideally corrected (immune correction) by the present inventors' immune refocusing strategies.

<Effect of N-Type Glycochain Introduced into gB Domain I>

In the gB variant, bcev19, modifications of D199N, D200A, H201T are introduced into domain I, and modifications of R613A, R567N, P568S, G569S, S631N, H632T, Q633T are introduced into domain IV. In bcev50, modifications of D199N, D200A, H201T are introduced into domain I, and modifications of R613A, R567N, P568S, G569S, S631N, H632T, Q633T, R602N, D603A, A604T are introduced into domain IV. To further investigate the effect of the modifications introduced into bcev19 and bcev50, variants bcev19' and bcev50' in which only modifications D199N, D200A, H201T of domain I contained in bcev19 and bcev50 returned to the amino acid sequences of the original, respectively, were made.

Transient expression using an Expi293 expression system was performed to compare the expression levels (Table 8). As the result, the expression levels of bcev19, bcev19', bcev50 and bcev50' were 10.81 µg/mL, 1.28 µg/mL, 6.29 µg/mL, and 4.36 µg/mL, respectively. When comparing the expression levels of bcev19 and bcev19', bcev19 was 8.45 times higher than bcev19', and when comparing the expression levels of bcev50 and bcev50', bcev50 was 1.44 times higher than bcev50'. This means that D199N, D200A, H201T in bcev19 and bcev50 are mutations that contribute to expression level enhancement. This is also supported by similar results obtained in bceg1-3 in which modification of D199N, D200A, H201T were introduced to gB1-705 (Table 4).

TABLE 8

| Clone | Mutation site | Yield (µg/mL) | Artificial glycochain introduction |
|---|---|---|---|
| bcev19 | D199N, D200A, H201T, R567N, P568S, G569S, R613A, S631N, H632T, Q633T | 10.81 | 3 |
| bcev19' | R567N, P568S, G569S, R613A, S631N, H632T, Q633T | 1.28 | 2 |
| bcev50 | D199N, D200A, H201T, R567N, P568S, G569S, R613A, R602N, D603A, A604T, S631N, H632T, Q633T | 6.29 | 4 |
| bcev50' | R567N, P568S, G569S, R613A, R602N, Q603A, A604T, S631N, H632T, Q633T | 4.36 | 3 |

Figure 14:
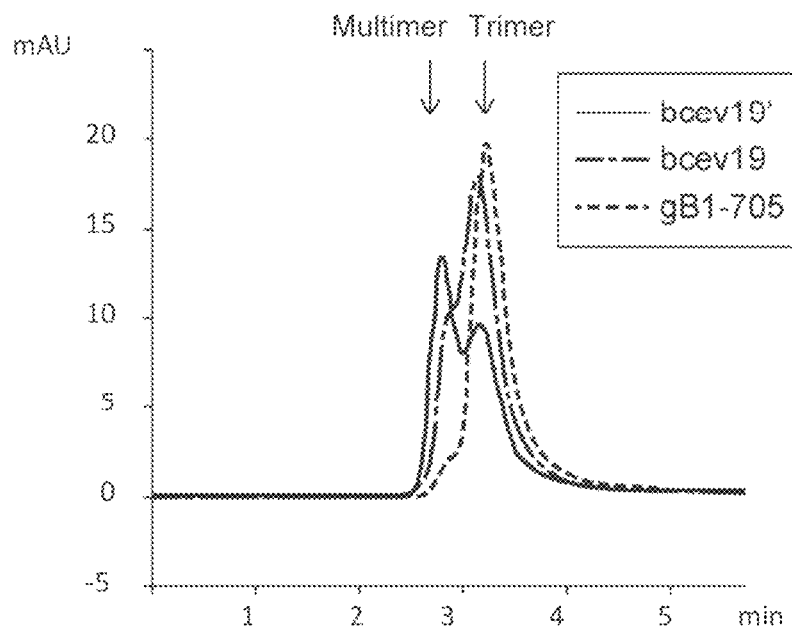
FIG. 14 is a diagram showing the result of property analysis of bcev19, bcev19', bcev50 and bcev50' by gel filtration chromatography in Example 5.
Figure 14:
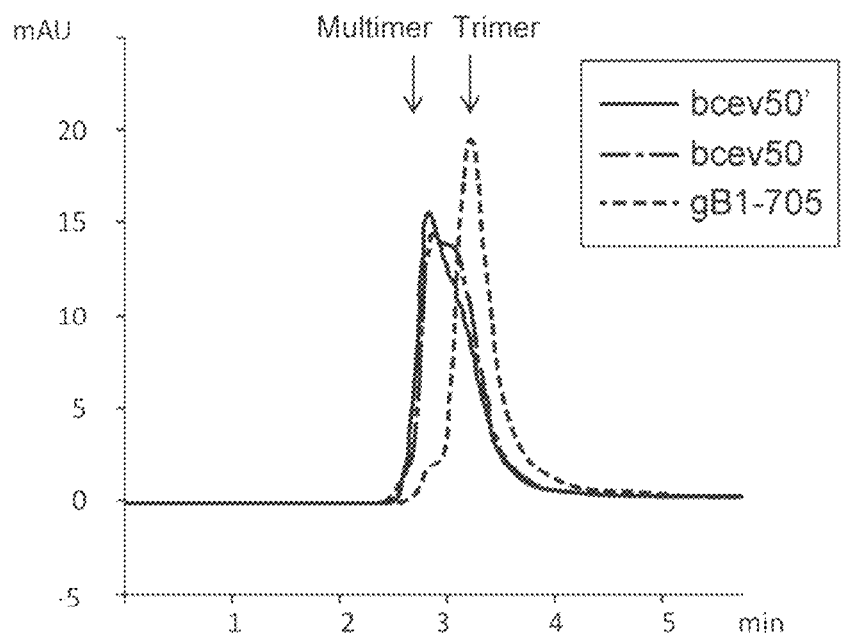

Furthermore, property analysis of bcev19, bcev19', bcev50 and bcev50' was performed by gel filtration chromatography. The result is shown in FIG. 14. The bcev19 had a higher native trimer content than bcev19' (FIG. 14(A)) and bcev50 had a higher trimer content than bcev50' (FIG.

14(B)). This means that D199N, D200A, H201T in bcev19 and bcev50 are mutations that contribute to property improvement.

Figure 16:
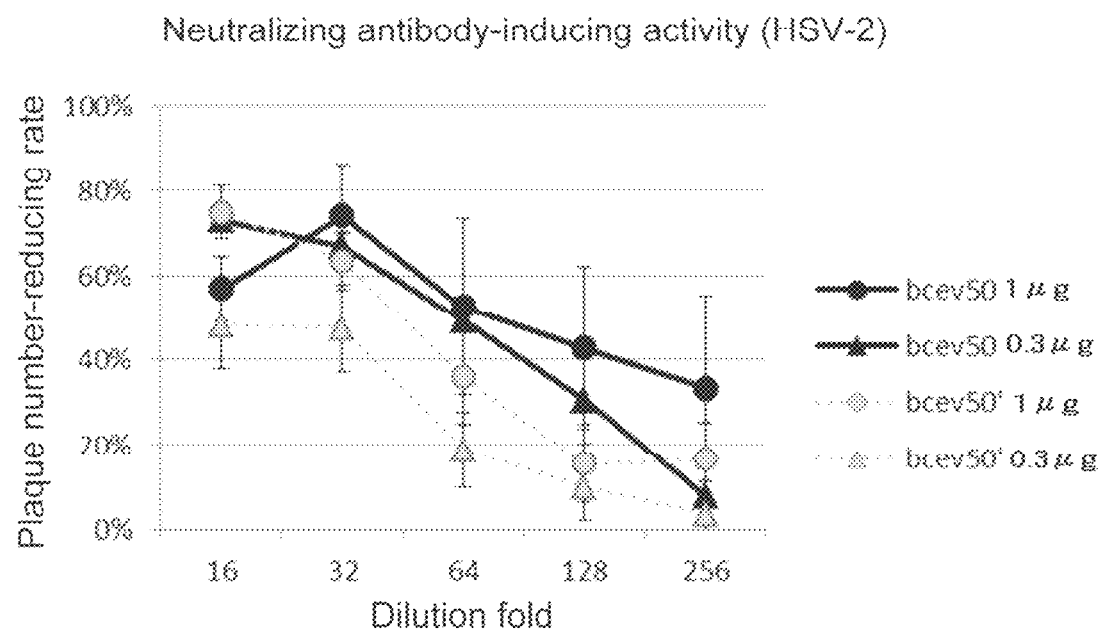
FIG. 16 is a diagram showing the comparison result of bcev50 and bcev50' in the mouse immunogenicity test of Example 5.
Figure 16:
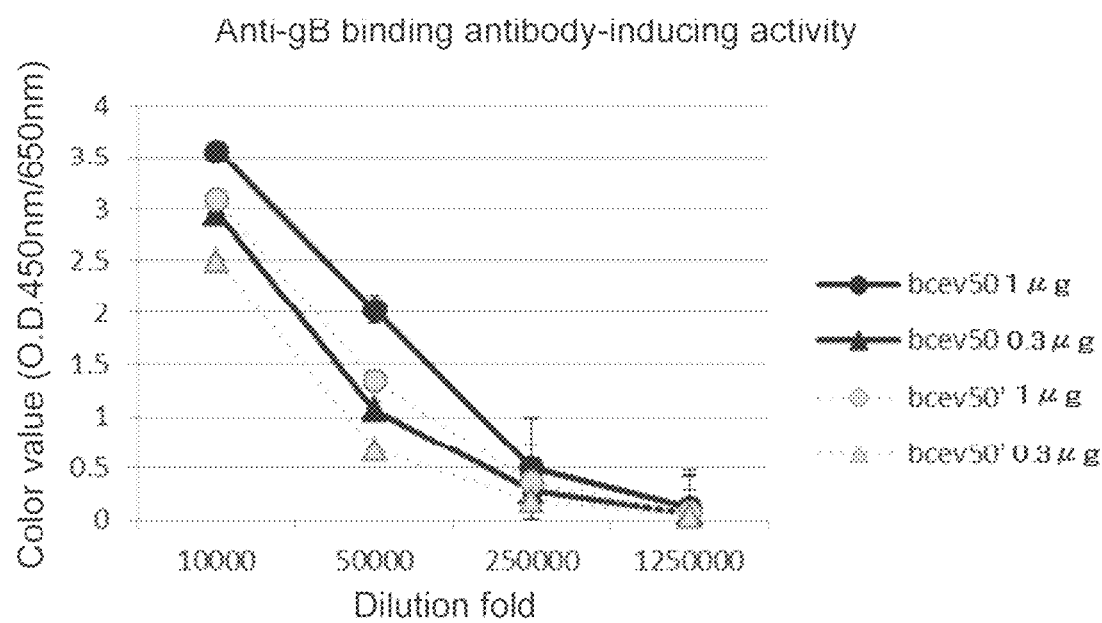

Next, bcev19 and bcev19', and bcev50 and bcev50' were respectively compared in mouse immunogenicity tests. Mice were subcutaneously immunized with antigen dose of 0.3 μg/mouse and 1 μg/mouse at 2-week intervals for 3 times. The experiment was performed setting the number of mouse cases in each group as n=4. A comparison of bcev19 and bcev19' is shown in FIG. 15, and a comparison of bcev50 and bcev50' is shown in FIG. 16, respectively (Mean values of n=4 are plotted with ±SE error bars in the graph). Using serum collected 2 weeks after final immunization, binding antibody-inducing activity against wild-type gB antigen (anti-gB ELISA) and neutralizing antibody-inducing activity against HSV-2 (plaque number-reducing rate) were evaluated. As the result, it was found in both indexes that higher antibody-inducing activity was tend to be exhibited for bcev19 than bcev19' and for bcev50 than bcev50'.

From the above results, it was found that among the mutations introduced into the variants bcev19 and bcev50, the N-type glycochains (D199N, D200A, H201T) of domain I are mutations that contribute not only to neutralizing antibody-inducing ability enhancement, but also to protein expression level enhancement and property improvement.

INDUSTRIAL APPLICABILITY

Modified HSV gB proteins of the present invention can be used in the production of vaccines effective for prevention and treatment of HSV infections.

The invention claimed is:

1. A modified protein of a herpes simplex virus 2 (HSV-2) envelope glycoprotein B (gB) (modified HSV-2 gB protein), wherein the modified HSV-2 gB protein is derived from a wild-type HSV gB set forth in SEQ ID NO:1,
wherein the wild-type HSV-2 gB protein is modified to introduce a N-type glycochain at one or more sites of interest by a substitution of an amino acid residue, a deletion of an amino acid residue, and/or a substitution or deletion of an amino acid residue, such that the three continuous amino acid sequence of the site of interest at which the N-type glycochain is introduced become NXS or NXT,
wherein the "X" in the consensus sequences NXS or NXT is any amino acid except a proline, and
wherein the one or more sites of interest are selected from the group consisting of amino acids residues D199, R567, R602 and S631 in the amino acid sequence set forth in SEQ ID NO:1.

2. The modified HSV-2 gB protein according to claim 1, wherein the modification includes a modification performed by a substitution of an amino acid residue and a deletion of an amino acid residue.

3. The modified HSV-2 gB protein according to claim 1, wherein the modification includes a modification performed by introducing a glycochain by the substitution or deletion of an amino acid residue.

4. The modified HSV-2 gB protein according to claim 1, wherein a N-type glycochain is introduced at one site of interest selected from the group consisting of amino acid residues D199, R567, R602 and S631 in the amino acid sequence set forth in SEQ ID NO: 1.

5. The modified HSV-2 gB protein according to claim 1, wherein a N-type glycochain is introduced at two or more sites of interest selected from the group consisting of amino acid residues D199, R567, R602 and S631 in the amino acid sequence set forth in SEQ ID NO: 1.

6. The modified HSV-2 gB protein according to claim 5, wherein the sites of interest are amino acid residues R567 and S631 in the amino acid sequence set forth in SEQ ID NO: 1.

7. The modified HSV-2 gB protein according to claim 6, comprising amino acid residue substitutions R567N, P568S, G569S, S631N, H632T and Q633T in the amino acid sequence set forth in SEQ ID NO: 1.

8. The modified HSV-2 gB protein according to claim 5, wherein the sites of interest are amino acid residues D199, R567 and S631 in the amino acid sequence set forth in SEQ ID NO: 1.

9. The modified HSV-2 gB protein according to claim 4, wherein the site of interest is amino acid residue R602 in the amino acid sequence set forth in SEQ ID NO: 1.

10. The modified HSV-2 gB protein according to claim 9, comprising amino acid residue substitutions R602N, D603A, A604T in the amino acid sequence set forth in SEQ ID NO: 1.

11. The modified HSV-2 gB protein according to claim 3, wherein the site of interest is amino acid residue D199 in the amino acid sequence set forth in SEQ ID NO: 1.

12. The modified HSV-2 gB protein according to claim 11, comprising amino acid residue substitutions D199N, D200A, and H201T in the amino acid sequence set forth in SEQ ID NO: 1.

13. The modified HSV-2 gB protein according to claim 2, comprising a substitution of an amino acid residue corresponding to an arginine at position 613 (R613) in the amino acid sequence set forth in SEQ ID NO: 1 with an alanine residue.

14. An HSV vaccine comprising the modified HSV-2 gB protein according to claim 1.

* * * * *

SEQUENCE LISTING

```
<160> NUMBER OF SEQ ID NOS: 4

<210> SEQ ID NO 1
<211> LENGTH: 705
<212> TYPE: PRT
<213> ORGANISM: Herpes simplex virus-2
<220> FEATURE:
<223> OTHER INFORMATION: HSV gB1-705

<400> SEQUENCE: 1

Ala Pro Ala Ala Pro Ala Ala Pro Arg Ala Ser Gly Gly Val Ala Ala
1               5                   10                  15

Thr Val Ala Ala Asn Gly Gly Pro Ala Ser Arg Pro Pro Pro Val Pro
            20                  25                  30

Ser Pro Ala Thr Thr Lys Ala Arg Lys Arg Lys Thr Lys Lys Pro Pro
        35                  40                  45

Lys Arg Pro Glu Ala Thr Pro Pro Pro Asp Ala Asn Ala Thr Val Ala
    50                  55                  60

Ala Gly His Ala Thr Leu Arg Ala His Leu Arg Glu Ile Lys Val Glu
65                  70                  75                  80

Asn Ala Asp Ala Gln Phe Tyr Val Cys Pro Pro Pro Thr Gly Ala Thr
                85                  90                  95

Val Val Gln Phe Glu Gln Pro Arg Arg Cys Pro Thr Arg Pro Glu Gly
            100                 105                 110

Gln Asn Tyr Thr Glu Gly Ile Ala Val Val Phe Lys Glu Asn Ile Ala
        115                 120                 125

Pro Tyr Lys Phe Lys Ala Thr Met Tyr Tyr Lys Asp Val Thr Val Ser
    130                 135                 140

Gln Val Trp Phe Gly His Arg Tyr Ser Gln Phe Met Gly Ile Phe Glu
145                 150                 155                 160

Asp Arg Ala Pro Val Pro Phe Glu Glu Val Ile Asp Lys Ile Asn Ala
                165                 170                 175

Lys Gly Val Cys Arg Ser Thr Ala Lys Tyr Val Arg Asn Asn Met Glu
            180                 185                 190

Thr Thr Ala Phe His Arg Asp Asp His Glu Thr Asp Met Glu Leu Lys
        195                 200                 205

Pro Ala Lys Val Ala Thr Arg Thr Ser Arg Gly Trp His Thr Thr Asp
    210                 215                 220

Leu Lys Tyr Asn Pro Ser Arg Val Glu Ala Phe His Arg Tyr Gly Thr
225                 230                 235                 240

Thr Val Asn Cys Ile Val Glu Glu Val Asp Ala Arg Ser Val Tyr Pro
```

```
                    245                 250                 255
Tyr Asp Glu Phe Val Leu Ala Thr Gly Asp Phe Val Tyr Met Ser Pro
                260                 265                 270

Phe Tyr Gly Tyr Arg Glu Gly Ser His Thr Glu His Thr Ser Tyr Ala
                275                 280                 285

Ala Asp Arg Phe Lys Gln Val Asp Gly Phe Tyr Ala Arg Asp Leu Thr
            290                 295                 300

Thr Lys Ala Arg Ala Thr Ser Pro Thr Arg Asn Leu Leu Thr Thr
305                 310                 315                 320

Pro Lys Phe Thr Val Ala Trp Asp Trp Val Pro Lys Arg Pro Ala Val
                325                 330                 335

Cys Thr Met Thr Lys Trp Gln Glu Val Asp Glu Met Leu Arg Ala Glu
                340                 345                 350

Tyr Gly Gly Ser Phe Arg Phe Ser Ser Asp Ala Ile Ser Thr Thr Phe
                355                 360                 365

Thr Thr Asn Leu Thr Gln Tyr Ser Leu Ser Arg Val Asp Leu Gly Asp
            370                 375                 380

Cys Ile Gly Arg Asp Ala Arg Glu Ala Ile Asp Arg Met Phe Ala Arg
385                 390                 395                 400

Lys Tyr Asn Ala Thr His Ile Lys Val Gly Gln Pro Gln Tyr Tyr Leu
                405                 410                 415

Ala Thr Gly Gly Phe Leu Ile Ala Tyr Gln Pro Leu Leu Ser Asn Thr
                420                 425                 430

Leu Ala Glu Leu Tyr Val Arg Glu Tyr Met Arg Glu Gln Asp Arg Lys
            435                 440                 445

Pro Arg Asn Ala Thr Pro Ala Pro Leu Arg Glu Ala Pro Ser Ala Asn
            450                 455                 460

Ala Ser Val Glu Arg Ile Lys Thr Thr Ser Ser Ile Glu Phe Ala Arg
465                 470                 475                 480

Leu Gln Phe Thr Tyr Asn His Ile Gln Arg His Val Asn Asp Met Leu
                485                 490                 495

Gly Arg Ile Ala Val Ala Trp Cys Glu Leu Gln Asn His Glu Leu Thr
                500                 505                 510

Leu Trp Asn Glu Ala Arg Lys Leu Asn Pro Asn Ala Ile Ala Ser Ala
            515                 520                 525

Thr Val Gly Arg Arg Val Ser Ala Arg Met Leu Gly Asp Val Met Ala
            530                 535                 540

Val Ser Thr Cys Val Pro Val Ala Pro Asp Asn Val Ile Val Gln Asn
545                 550                 555                 560

Ser Met Arg Val Ser Ser Arg Pro Gly Thr Cys Tyr Ser Arg Pro Leu
                565                 570                 575

Val Ser Phe Arg Tyr Glu Asp Gln Gly Pro Leu Ile Glu Gly Gln Leu
                580                 585                 590

Gly Glu Asn Asn Glu Leu Arg Leu Thr Arg Asp Ala Leu Glu Pro Cys
            595                 600                 605

Thr Val Gly His Arg Arg Tyr Phe Ile Phe Gly Gly Gly Tyr Val Tyr
            610                 615                 620

Phe Glu Glu Tyr Ala Tyr Ser His Gln Leu Ser Arg Ala Asp Val Thr
625                 630                 635                 640

Thr Val Ser Thr Phe Ile Asp Leu Asn Ile Thr Met Leu Glu Asp His
                645                 650                 655

Glu Phe Val Pro Leu Glu Val Tyr Thr Arg His Glu Ile Lys Asp Ser
                660                 665                 670
```

```
Gly Leu Leu Asp Tyr Thr Glu Val Gln Arg Arg Asn Gln Leu His Asp
            675                 680                 685

Leu Arg Phe Ala Asp Ile Asp Thr Val Ile Arg Ala Asp Ala Asn Ala
            690                 695                 700

Ala
705

<210> SEQ ID NO 2
<211> LENGTH: 904
<212> TYPE: PRT
<213> ORGANISM: Herpes simplex virus-1

<400> SEQUENCE: 2

Met His Gln Gly Ala Pro Ser Trp Gly Arg Arg Trp Phe Val Val Trp
1               5                   10                  15

Ala Leu Leu Gly Leu Thr Leu Gly Val Leu Val Ala Ser Ala Ala Pro
                20                  25                  30

Thr Ser Pro Gly Thr Pro Gly Val Ala Ala Ala Thr Gln Ala Ala Asn
            35                  40                  45

Gly Gly Pro Ala Thr Pro Ala Pro Pro Ala Pro Gly Ala Ala Pro Thr
        50                  55                  60

Gly Asp Pro Lys Pro Lys Lys Asn Lys Lys Pro Lys Asn Pro Thr Pro
65                  70                  75                  80

Pro Arg Pro Ala Gly Asp Asn Ala Thr Val Ala Ala Gly His Ala Thr
                85                  90                  95

Leu Arg Glu His Leu Arg Asp Ile Lys Ala Glu Asn Thr Asp Ala Asn
            100                 105                 110

Phe Tyr Val Cys Pro Pro Pro Thr Gly Ala Thr Val Val Gln Phe Glu
        115                 120                 125

Gln Pro Arg Arg Cys Pro Thr Arg Pro Glu Gly Gln Asn Tyr Thr Glu
    130                 135                 140

Gly Ile Ala Val Val Phe Lys Glu Asn Ile Ala Pro Tyr Lys Phe Lys
145                 150                 155                 160

Ala Thr Met Tyr Tyr Lys Asp Val Thr Val Ser Gln Val Trp Phe Gly
                165                 170                 175

His Arg Tyr Ser Gln Phe Met Gly Ile Phe Glu Asp Arg Ala Pro Val
            180                 185                 190

Pro Phe Glu Glu Val Ile Asp Lys Ile Asn Ala Lys Gly Val Cys Arg
        195                 200                 205

Ser Thr Ala Lys Tyr Val Arg Asn Asn Leu Glu Thr Thr Ala Phe His
    210                 215                 220

Arg Asp Asp His Glu Thr Asp Met Glu Leu Lys Pro Ala Asn Ala Ala
225                 230                 235                 240

Thr Arg Thr Ser Arg Gly Trp His Thr Thr Asp Leu Lys Tyr Asn Pro
                245                 250                 255

Ser Arg Val Glu Ala Phe His Arg Tyr Gly Thr Thr Val Asn Cys Ile
            260                 265                 270

Val Glu Glu Val Asp Ala Arg Ser Val Tyr Pro Tyr Asp Glu Phe Val
        275                 280                 285

Leu Ala Thr Gly Asp Phe Val Tyr Met Ser Pro Phe Tyr Gly Tyr Arg
    290                 295                 300

Glu Gly Ser His Thr Glu His Thr Thr Tyr Ala Ala Asp Arg Phe Lys
305                 310                 315                 320

Gln Val Asp Gly Phe Tyr Ala Arg Asp Leu Thr Thr Lys Ala Arg Ala
```

```
            325                 330                 335
Thr Ala Pro Thr Thr Arg Asn Leu Leu Thr Thr Pro Lys Phe Thr Val
            340                 345                 350
Ala Trp Asp Trp Val Pro Lys Arg Pro Ser Val Cys Thr Met Thr Lys
            355                 360                 365
Trp Gln Glu Val Asp Glu Met Leu Arg Ser Glu Tyr Gly Gly Ser Phe
370                 375                 380
Arg Phe Ser Ser Asp Ala Ile Ser Thr Thr Phe Thr Thr Asn Leu Thr
385                 390                 395                 400
Glu Tyr Pro Leu Ser Arg Val Asp Leu Gly Asp Cys Ile Gly Lys Asp
            405                 410                 415
Ala Arg Asp Ala Met Asp Arg Ile Phe Ala Arg Arg Tyr Asn Ala Thr
            420                 425                 430
His Ile Lys Val Gly Gln Pro Gln Tyr Tyr Gln Ala Asn Gly Gly Phe
            435                 440                 445
Leu Ile Ala Tyr Gln Pro Leu Leu Ser Asn Thr Leu Ala Glu Leu Tyr
            450                 455                 460
Val Arg Glu His Leu Arg Glu Gln Ser Arg Lys Pro Pro Asn Pro Thr
465                 470                 475                 480
Pro Pro Pro Gly Ala Ser Ala Asn Ala Ser Val Glu Arg Ile Lys
            485                 490                 495
Thr Thr Ser Ser Ile Glu Phe Ala Arg Leu Gln Phe Thr Tyr Asn His
            500                 505                 510
Ile Gln Arg His Val Asn Asp Met Leu Gly Arg Val Ala Ile Ala Trp
            515                 520                 525
Cys Glu Leu Gln Asn His Glu Leu Thr Leu Trp Asn Glu Ala Arg Lys
            530                 535                 540
Leu Asn Pro Asn Ala Ile Ala Ser Val Thr Val Gly Arg Arg Val Ser
545                 550                 555                 560
Ala Arg Met Leu Gly Asp Val Met Ala Val Ser Thr Cys Val Pro Val
            565                 570                 575
Ala Ala Asp Asn Val Ile Val Gln Asn Ser Met Arg Ile Ser Ser Arg
            580                 585                 590
Pro Gly Ala Cys Tyr Ser Arg Pro Leu Val Ser Phe Arg Tyr Glu Asp
            595                 600                 605
Gln Gly Pro Leu Val Glu Gly Gln Leu Gly Glu Asn Asn Glu Leu Arg
            610                 615                 620
Leu Thr Arg Asp Ala Ile Glu Pro Cys Thr Val Gly His Arg Arg Tyr
625                 630                 635                 640
Phe Thr Phe Gly Gly Gly Tyr Val Tyr Phe Glu Glu Tyr Ala Tyr Ser
            645                 650                 655
His Gln Leu Ser Arg Ala Asp Ile Thr Thr Val Ser Thr Phe Ile Asp
            660                 665                 670
Leu Asn Ile Thr Met Leu Glu Asp His Glu Phe Val Pro Leu Glu Val
            675                 680                 685
Tyr Thr Arg His Glu Ile Lys Asp Ser Gly Leu Leu Asp Tyr Thr Glu
            690                 695                 700
Val Gln Arg Arg Asn Gln Leu His Asp Leu Arg Phe Ala Asp Ile Asp
705                 710                 715                 720
Thr Val Ile His Ala Asp Ala Asn Ala Ala Met Phe Ala Gly Leu Gly
            725                 730                 735
Ala Phe Phe Glu Gly Met Gly Asp Leu Gly Arg Ala Val Gly Lys Val
            740                 745                 750
```

```
Val Met Gly Ile Val Gly Gly Val Ser Ala Val Ser Gly Val Ser
        755                 760                 765

Ser Phe Met Ser Asn Pro Phe Gly Ala Leu Ala Val Gly Leu Leu Val
770                 775                 780

Leu Ala Gly Leu Ala Ala Ala Phe Phe Ala Phe Arg Tyr Val Met Arg
785                 790                 795                 800

Leu Gln Ser Asn Pro Met Lys Ala Leu Tyr Pro Leu Thr Thr Lys Glu
                805                 810                 815

Leu Lys Asn Pro Thr Asn Pro Asp Ala Ser Gly Glu Gly Glu Glu Gly
                820                 825                 830

Gly Asp Phe Asp Glu Ala Lys Leu Ala Glu Ala Arg Glu Met Ile Arg
                835                 840                 845

Tyr Met Ala Leu Val Ser Ala Met Glu Arg Thr Glu His Lys Ala Lys
        850                 855                 860

Lys Lys Gly Thr Ser Ala Leu Leu Ser Ala Lys Val Thr Asp Met Val
865                 870                 875                 880

Met Arg Lys Arg Arg Asn Thr Asn Tyr Thr Gln Val Pro Asn Lys Asp
                885                 890                 895

Gly Asp Ala Asp Glu Asp Asp Leu
            900

<210> SEQ ID NO 3
<211> LENGTH: 946
<212> TYPE: PRT
<213> ORGANISM: Herpes simplex virus-2

<400> SEQUENCE: 3

Met Arg Gly Gly Gly Leu Ile Cys Ala Leu Val Val Gly Ala Leu Val
1               5                   10                  15

Ala Ala Val Ala Ser Ala Ala Pro Ala Ala Pro Ala Ala Pro Arg Ala
                20                  25                  30

Ser Gly Gly Val Ala Ala Thr Val Ala Ala Asn Gly Gly Pro Ala Ser
            35                  40                  45

Arg Pro Pro Pro Val Pro Ser Pro Ala Thr Thr Lys Ala Arg Lys Arg
50                  55                  60

Lys Thr Lys Lys Pro Pro Lys Arg Pro Glu Ala Thr Pro Pro Pro Asp
65                  70                  75                  80

Ala Asn Ala Thr Val Ala Ala Gly His Ala Thr Leu Arg Ala His Leu
                85                  90                  95

Arg Glu Ile Lys Val Glu Asn Ala Asp Ala Gln Phe Tyr Val Cys Pro
            100                 105                 110

Pro Pro Thr Gly Ala Thr Val Val Gln Phe Glu Gln Pro Arg Arg Cys
        115                 120                 125

Pro Thr Arg Pro Glu Gly Gln Asn Tyr Thr Glu Gly Ile Ala Val Val
    130                 135                 140

Phe Lys Glu Asn Ile Ala Pro Tyr Lys Phe Lys Ala Thr Met Tyr Tyr
145                 150                 155                 160

Lys Asp Val Thr Val Ser Gln Val Trp Phe Gly His Arg Tyr Ser Gln
                165                 170                 175

Phe Met Gly Ile Phe Glu Asp Arg Ala Pro Val Pro Phe Glu Glu Val
            180                 185                 190

Ile Asp Lys Ile Asn Ala Lys Gly Val Cys Arg Ser Thr Ala Lys Tyr
        195                 200                 205

Val Arg Asn Asn Met Glu Thr Thr Ala Phe His Arg Asp Asp His Glu
```

```
                    210                 215                 220
Thr Asp Met Glu Leu Lys Pro Ala Lys Val Ala Thr Arg Thr Ser Arg
225                 230                 235                 240

Gly Trp His Thr Thr Asp Leu Lys Tyr Asn Pro Ser Arg Val Glu Ala
                    245                 250                 255

Phe His Arg Tyr Gly Thr Thr Val Asn Cys Ile Val Glu Glu Val Asp
                260                 265                 270

Ala Arg Ser Val Tyr Pro Tyr Asp Glu Phe Val Leu Ala Thr Gly Asp
            275                 280                 285

Phe Val Tyr Met Ser Pro Phe Tyr Gly Tyr Arg Glu Gly Ser His Thr
        290                 295                 300

Glu His Thr Ser Tyr Ala Ala Asp Arg Phe Lys Gln Val Asp Gly Phe
305                 310                 315                 320

Tyr Ala Arg Asp Leu Thr Thr Lys Ala Arg Ala Thr Ser Pro Thr Thr
                325                 330                 335

Arg Asn Leu Leu Thr Thr Pro Lys Phe Thr Val Ala Trp Asp Trp Val
                340                 345                 350

Pro Lys Arg Pro Ala Val Cys Thr Met Thr Lys Trp Gln Glu Val Asp
            355                 360                 365

Glu Met Leu Arg Ala Glu Tyr Gly Gly Ser Phe Arg Phe Ser Ser Asp
        370                 375                 380

Ala Ile Ser Thr Thr Phe Thr Thr Asn Leu Thr Gln Tyr Ser Leu Ser
385                 390                 395                 400

Arg Val Asp Leu Gly Asp Cys Ile Gly Arg Asp Ala Arg Glu Ala Ile
                405                 410                 415

Asp Arg Met Phe Ala Arg Lys Tyr Asn Ala Thr His Ile Lys Val Gly
                420                 425                 430

Gln Pro Gln Tyr Tyr Leu Ala Thr Gly Gly Phe Leu Ile Ala Tyr Gln
            435                 440                 445

Pro Leu Leu Ser Asn Thr Leu Ala Glu Leu Tyr Val Arg Glu Tyr Met
        450                 455                 460

Arg Glu Gln Asp Arg Lys Pro Arg Asn Ala Thr Pro Ala Pro Leu Arg
465                 470                 475                 480

Glu Ala Pro Ser Ala Asn Ala Ser Val Glu Arg Ile Lys Thr Thr Ser
                485                 490                 495

Ser Ile Glu Phe Ala Arg Leu Gln Phe Thr Tyr Asn His Ile Gln Arg
                500                 505                 510

His Val Asn Asp Met Leu Gly Arg Ile Ala Val Ala Trp Cys Glu Leu
            515                 520                 525

Gln Asn His Glu Leu Thr Leu Trp Asn Glu Ala Arg Lys Leu Asn Pro
        530                 535                 540

Asn Ala Ile Ala Ser Ala Thr Val Gly Arg Arg Val Ser Ala Arg Met
545                 550                 555                 560

Leu Gly Asp Val Met Ala Val Ser Thr Cys Val Pro Val Ala Pro Asp
                565                 570                 575

Asn Val Ile Val Gln Asn Ser Met Arg Val Ser Ser Arg Pro Gly Thr
                580                 585                 590

Cys Tyr Ser Arg Pro Leu Val Ser Phe Arg Tyr Glu Asp Gln Gly Pro
            595                 600                 605

Leu Ile Glu Gly Gln Leu Gly Glu Asn Asn Glu Leu Arg Leu Thr Arg
        610                 615                 620

Asp Ala Leu Glu Pro Cys Thr Val Gly His Arg Arg Tyr Phe Ile Phe
625                 630                 635                 640
```

Gly Gly Gly Tyr Val Tyr Phe Glu Glu Tyr Ala Tyr Ser His Gln Leu
            645                 650                 655

Ser Arg Ala Asp Val Thr Thr Val Ser Thr Phe Ile Asp Leu Asn Ile
            660                 665                 670

Thr Met Leu Glu Asp His Glu Phe Val Pro Leu Glu Val Tyr Thr Arg
            675                 680                 685

His Glu Ile Lys Asp Ser Gly Leu Leu Asp Tyr Thr Glu Val Gln Arg
            690                 695                 700

Arg Asn Gln Leu His Asp Leu Arg Phe Ala Asp Ile Asp Thr Val Ile
705                 710                 715                 720

Arg Ala Asp Ala Asn Ala Ala Met Phe Ala Gly Leu Cys Ala Phe Phe
                725                 730                 735

Glu Gly Met Gly Asp Leu Gly Arg Ala Val Gly Lys Val Val Met Gly
            740                 745                 750

Val Val Gly Gly Val Val Ser Ala Val Ser Gly Val Ser Ser Phe Met
            755                 760                 765

Ser Asn Pro Phe Gly Ala Leu Ala Val Gly Leu Leu Val Leu Ala Gly
            770                 775                 780

Leu Val Ala Ala Phe Phe Ala Phe Arg Tyr Val Leu Gln Leu Gln Arg
785                 790                 795                 800

Asn Pro Met Lys Ala Leu Tyr Pro Leu Thr Thr Lys Glu Leu Lys Thr
                805                 810                 815

Ser Asp Pro Gly Gly Val Gly Gly Glu Gly Glu Gly Ala Glu Gly
            820                 825                 830

Gly Gly Phe Asp Glu Ala Lys Leu Ala Glu Ala Arg Glu Met Ile Arg
            835                 840                 845

Tyr Met Ala Leu Val Ser Ala Met Glu Arg Thr Glu His Lys Ala Arg
850                 855                 860

Lys Lys Gly Thr Ser Ala Leu Leu Ser Ser Lys Val Thr Asn Met Val
865                 870                 875                 880

Leu Arg Lys Arg Asn Lys Ala Arg Tyr Ser Pro Leu His Asn Glu Asp
                885                 890                 895

Glu Ala Gly Asp Glu Asp Glu Leu Ala Arg Lys Lys Gly Thr Ser Ala
            900                 905                 910

Leu Leu Ser Ser Lys Val Thr Asn Met Val Leu Arg Lys Arg Asn Lys
            915                 920                 925

Ala Arg Tyr Ser Pro Leu His Asn Glu Asp Glu Ala Gly Asp Glu Asp
            930                 935                 940

Glu Leu
945

<210> SEQ ID NO 4
<211> LENGTH: 2712
<212> TYPE: DNA
<213> ORGANISM: Herpes simplex virus-2

<400> SEQUENCE: 4
atgcgcgggg ggggcttgat ttgcgcgctg gtcgtggggg cgctggtggc cgcggtggcg      60
tcggcggccc cggcggcccc ggcggccccc cgcgcctcgg gcggcgtggc cgcgaccgtc     120
gcggcgaacg ggggtcccgc ctcccggccg cccccgtcc cgagcccgc gaccaccaag      180 gcccggaagc ggaaaaccaa aaagccgccc aagcggcccg aggcgacccc gccccccgac     240
gccaacgcga ccgtcgccgc cggccacgcc acgctgcgcg cgcacctgcg ggaaatcaag     300

```
gtcgagaacg ccgatgccca gttttacgtg tgcccgcccc cgacgggcgc cacggtggtg      360
cagtttgagc agccgcgccg ctgcccgacg cgcccggagg ggcagaacta cacggagggc      420
atcgcggtgg tcttcaagga gaacatcgcc ccgtacaaat tcaaggccac catgtactac      480
aaagacgtga ccgtgtcgca ggtgtggttc ggccaccgct actcccagtt tatggggata      540
ttcgaggacc gcgcccccgt tcccttcgag gaggtgatcg acaagattaa cgccaagggg      600
gtctgccgct ccacggccaa gtacgtgcgg aacaacatgg agaccaccgc gtttcaccgg      660
gacgaccacg agaccgacat ggagctcaag ccggcgaagg tcgccacgcg cacgagccgg      720
gggtggcaca ccaccgacct caagtacaac ccctcgcggg tggaggcgtt ccatcggtac      780
ggcacgacgg tcaactgcat cgtcgaggag gtggacgcgc ggtcggtgta cccgtacgat      840
gagtttgtgt ggcgacgggc cgactttgtg tacatgtccc cgttttacgg ctaccgggag      900
gggtcgcaca ccgagcacac cagctacgcc gccgaccgct caagcaggt cgacggcttc      960 tacgcgcgcg acctcaccac gaaggcccgg ccacgtcgc cgacgacccg caacttgctg      1020 acgacccca gtttaccgt ggcctgggac tgggtgccga agcgaccggc ggtctgcacc      1080
atgaccaagt ggcaggaggt ggacgagatg ctccgcgccg agtacggcgg ctccttccgc      1140
ttctcctccg acgccatctc gaccaccttc accaccaacc tgacccagta ctcgctctcg      1200
cgcgtcgacc tgggcgactg cattggccgg gatgcccgcg aggccatcga ccgcatgttt      1260
gcgcgcaagt acaacgccac gcacatcaag gtgggccagc cgcagtacta cctggccacg      1320
gggggcttcc tcatcgcgta ccagcccctc ctcagcaaca cgctcgccga gctgtacgtg      1380
cgggagtaca tgcgggagca ggaccgcaag ccccggaatg ccacgcccgc gccactgcgg      1440
gaggcgccca gcgccaacgc gtccgtggag cgcatcaaga ccacctcctc gatcgagttc      1500
gcccggctgc agtttacgta taaccacata cagcgccacg tgaacgacat gctggggcgc      1560
atcgccgtcg cgtggtgcga gctgcagaac cacgagctga ctctctggaa cgaggcccgc      1620
aagctcaacc ccaacgccat cgcctccgcc accgtcggcc ggcgggtgag cgcgcgcatg      1680
ctcggagacg tcatggccgt ctccacgtgc gtgcccgtcg ccccgacaa cgtgatcgtg      1740 cagaactcga tgcgcgtcag ctcgcggccg gggacgtgct acagccgccc cctggtcagc      1800
tttcggtacg aagaccaggg cccgctgatc gaggggcagc tgggcgagaa caacgagctg      1860
cgcctcaccc gcgacgcgct cgagccgtgc accgtgggcc accggcgcta cttcatcttc      1920
ggcgggggct acgtgtactt cgaggagtac gcgtactctc accagctgag tcgcgccgac      1980
gtcaccaccg tcagcacctt catcgacctg aacatcacca tgctggagga ccacgagttt      2040
gtgcccctgg aggtctacac gcgccacgag atcaaggaca gcggcctgct ggactacacg      2100
gaggtccagc gccgcaacca gctgcacgac ctgcgctttg ccgacatcga cacggtcatc      2160
cgcgccgacg ccaacgccgc catgttcgcg gggctgtgcg cgttcttcga ggggatgggg      2220
gacttggggc gcgcggtcgg caaggtagtc atgggagtag tggggggcgt ggtgtcggcc      2280
gtctcggggc tgtcctcctt tatgtccaac cccttcgggg cgcttgccgt ggggctgctg      2340
gtcctggccg gcctggtcgc ggccttcttc gccttccgct acgtcctgca actgcaacgc      2400
aatcccatga aggccctgta ccgctcacc accaaggaac tcaagacttc cgaccccggg      2460
ggcgtgggcg ggggaggggg aggaaggcgcg gagggggcg ggtttgacga ggccaagttg      2520
gccgaggccc gagaaatgat ccgatatatg gctttggtgt cggccatgga gcgcacggaa      2580
```

-continued

```
cacaaggcca gaaagaaggg cacgagcgcc ctgctcagct ccaaggtcac caacatggtt    2640
ctgcgcaagc gcaacaaagc caggtactct ccgctccaca acgaggacga ggccggagac    2700
gaagacgagc tc                                                        2712
```